(12) United States Patent
Xu

(10) Patent No.: US 9,149,618 B2
(45) Date of Patent: Oct. 6, 2015

(54) BUILT-IN NON-VERBAL INSTRUCTIONAL DEVICE INTEGRATABLE TO APPLICATORS

(75) Inventor: Bai Xu, Slingerlands, NY (US)

(73) Assignee: NANOMED SKINCARE, INC., Albany, NY (US)

( * ) Notice: Subject to any disclaimer, the term of this patent is extended or adjusted under 35 U.S.C. 154(b) by 412 days.

(21) Appl. No.: 13/634,815

(22) PCT Filed: Mar. 17, 2010

(86) PCT No.: PCT/US2010/000800
§ 371 (c)(1),
(2), (4) Date: Nov. 15, 2012

(87) PCT Pub. No.: WO2011/115602
PCT Pub. Date: Sep. 22, 2011

(65) Prior Publication Data
US 2013/0053752 A1  Feb. 28, 2013

(51) Int. Cl.
*A61B 17/20* (2006.01)
*A61M 37/00* (2006.01)
(Continued)

(52) U.S. Cl.
CPC .......... *A61M 37/0015* (2013.01); *A61B 17/205* (2013.01); *A61B 19/026* (2013.01);
(Continued)

(58) Field of Classification Search
CPC ............... A61B 2017/00115; A61B 2019/465; A61B 2019/4815; A61K 9/0021; A61M 2037/0023; A61M 2205/581; A61M 2205/582; A61M 2205/583; A61M 37/0015
USPC .......................................................... 604/46
See application file for complete search history.

(56) References Cited

U.S. PATENT DOCUMENTS

2006/0229562 A1* 10/2006 Marsh et al. ............. 604/164.01
2008/0214987 A1*  9/2008 Xu .................................. 604/21
(Continued)

FOREIGN PATENT DOCUMENTS

JP        2006527008 A    11/2006
JP        2008535636 A     9/2008
(Continued)

OTHER PUBLICATIONS

Written Opinion re: Singapore Application No. 201206908-4 dated Dec. 9, 2013 four (4) pages (English).
Notice of Reasons for Rejection re: Japanese Application No. JP 2013-500030 three (3) pages (Japanese).
Translation of Notice of Reasons for Rejection re: Japanese Application No. JP 2013-500030 three (3) pages (English).

*Primary Examiner* — Kevin C Sirmons
*Assistant Examiner* — Deanna K Hall
(74) *Attorney, Agent, or Firm* — Nath, Goldberg & Meyer; Joshua B. Goldberg

(57) ABSTRACT

A built-in non-verbal compact instructional device integratable to an applicator having a microdevice for painlessly perforating skin and optionally an active agent for application to the perforated area. The microdevice can include microneedles, microneedle arrays, microblades, microblade arrays, microknives, microknife arrays, and Functional MicroArrays (FMAs). The active agent can be stored in a first chamber. The microdevice can perforate stratum corneum without significant pain or discomfort to a patient. The active agent is applied to the perforated area. The device verifies compliance with predetermined methods of use, such as a light to indicate application with the recommended amount of force for perforating skin. The applicator can provide enhanced delivery of an active agent, with minimal discomfort, for therapeutic or cosmetic treatment, such as topical treatment for acne, or other skin disorders, wrinkles, blemishes, etc. The applicator is also useful for providing improved systemic or localized delivery of an active agent.

19 Claims, 20 Drawing Sheets

(51) Int. Cl.
*A61K 9/00* (2006.01)
*A61K 9/06* (2006.01)
*A61B 19/02* (2006.01)
*A61B 17/00* (2006.01)
*A61B 19/00* (2006.01)

(52) U.S. Cl.
CPC ............... *A61K9/0021* (2013.01); *A61K 9/06* (2013.01); *A61B 19/0256* (2013.01); *A61B 2017/00115* (2013.01); *A61B 2019/465* (2013.01); *A61B 2019/4815* (2013.01); *A61M 2037/0023* (2013.01); *A61M 2205/276* (2013.01); *A61M 2205/581* (2013.01); *A61M 2205/582* (2013.01); *A61M 2205/583* (2013.01)

(56) References Cited

U.S. PATENT DOCUMENTS

2008/0287858 A1* 11/2008 Duan .............................. 604/21
2008/0319370 A1* 12/2008 Wolpert et al. ................. 604/20
2009/0093757 A1    4/2009 Tennican

FOREIGN PATENT DOCUMENTS

| JP | 2008539010 A | 11/2008 |
| JP | 2008543510 A | 12/2008 |
| JP | 2009528874 A | 8/2009 |

* cited by examiner

003 IS MOVABLE. WHEN 003 IS APPLIED TO SKIN, IT DISPLACED IN THE DIRECTION SHOWN BY RED ARROW, CAUSING A SOUND, OR A LIGHT TO INDICATE SUCCESSFUL PRE-TREATMENT.

3D ILLUSTRATION OF APPLICATOR
IN ITS PACKAGED BOX

BUILT-IN NON-VERBAL INSTRUCTIONAL DEVICE INTEGRATABLE TO APPLICATORS

This is a National Phase Application filed under 35 U.S.C. 371 as a national stage of PCT/US2010/000800, filed Mar. 17, 2010, the content of which is hereby incorporated by reference in its entirety.

FIELD OF THE INVENTION

The present subject matter relates to a built-in non-verbal compact instructional device integratable to an applicator having a microdevice for painlessly perforating the skin and optionally an active agent for application to the area of skin being perforated. The microdevice of the applicator referred to herein can include microneedles, microneedle arrays, microblades, microblade arrays, microknives, microknife arrays, and Functional MicroArrays (FMAs).

BACKGROUND OF THE INVENTION

Drugs are commonly administered in solid form through pills or capsules that can be orally taken. However, many biological drugs can not be administered this way because of degradation in the gastrointestinal tract and quick elimination by the liver. Another common technique for administration of drugs in liquid form is through injection using a metal hypodermic needle that can cause significant pain and discomfort to patients. A number of physical and chemical techniques including electroporation, laser ablation, ultrasound, thermal, iontophoresis and chemical enhancers have been explored to develop painless percutaneous drug delivery techniques. It was found that it is very difficult for molecules with a molecular weight higher than 500 or a diameter larger than 1 nm to penetrate normal human skin.

Further studies showed that the key barrier for percutaneous delivery of substances is the stratum corneum layer, the outer layer of skin, that is about 4-30 micron thick. Invasive methods to overcome this skin barrier have been used in practice, such as intradermal (ID), intramuscular (IM) or subcutaneous (SC) injection using standard hypodermic needles and syringes. These methods cause pain and require a skilled professional. In addition, they may cause needle injuries. Similarly, current methods of extracting biologic fluids such as blood from patients suffer from the same disadvantages.

In order to improve the skin permeability of such therapeutic agents and other active ingredients, microneedles have been recently developed to disrupt the stratum corneum and facilitate the delivery of the active agents and ingredients to the epidermis. These active substances can then diffuse through the rest of the epidermis to the dermis to be absorbed by blood vessels and lymphatics. The substance absorbed can then get into the circulation system. Thus, both topical and systemic delivery of drugs is possible. Since there are no nerves and blood vessels in the stratum corneum and epidermis, this is a minimally invasive, painless and blood-free method of drug delivery. An additional advantage of this method, when engineered for topical delivery of vaccines, can lead to enhanced inoculation effect because the epidermis is rich in antigen presenting cells and is a desired target for vaccine delivery.

The prior art reports many devices and methods to overcome the skin barriers. For example, U.S. Pat. Nos. 5,855,801 and 5,928,207 assigned to The Regents of the University of California taught a microneedle fabrication method similar to IC compatible neural recording arrays. The disclosed microneedle arrays are typically linear arrays as they are in the plane of the silicon substrate surface. Microneedles have also been fabricated by heating the glass tube and lengthening the heated part till the diameter of the tip is reduced to the desired range. However, in general it is very difficult to control the size of the needle shaft and the tip this way, although biologists are still using this method to produce microneedles that can inject or withdraw substances from a single cell.

U.S. Pat. No. 6,503,231 by Prausnitz et al discloses a method for making out-of-the-plane porous or hollow microneedles. It either involves porous silicon formed by anodization of silicon or deals with sacrificial molds or selective removal of substrate materials to form fluidic conduits. U.S. Pat. No. 6,511,463 by JDS Uniphase Corp. also teaches a method to fabricate the same. U.S. Pat. No. 6,558,361 assigned to Nanopass Ltd. teaches a method for the manufacture of hollow microneedle arrays by removing a selective area of substrate material. U.S. Pat. No. 6,603,987 assigned to Bayer Corp. also discloses a method to make a hollow microneedle patch. All these methods are trying to perform certain functions of the current hypodermic needles and create a miniaturized analog to perform drug delivery or extract body fluids without causing pain and discomfort.

More recently, U.S. application publication No. 2004/0199103 describes a single-step method of delivering an active agent using a "solid solution perforator" ("SSP") which incorporates an active agent in the SSP matrix material itself. The SSP perforates the skin and then the SSP biodegrades and dissolves to release the active agent through the skin. The publication describes that the delivery of the active agent is initiated only after the SSP sufficiently degrades, and delivery is stopped once the SSP is removed from the skin.

U.S. application publication No. 2004/0241965 describes a method of making high aspect ratio electrode arrays comprised of solid metals. It involves the preparation of porous microchannel glass template, electrodeposition of metals in the microchannels, and final preparation of an electrode array following an electrodeposition. The body of microelectrode is formed by electrodeposition method similar to those used in forming nanowires. Microneedles having hollow bodies also require a readily available active agent reservoir or conduit for providing subsequent injection delivery of an active agent.

The prior methods to make microneedles, whether they are in-the-plane or out-of-the-plane from the substrate material, are cumbersome and/or expensive. The hollow microneedle arrays, while their sizes are scaled down from conventional needles, are especially expensive to make and use because of complexity in the fabrication process and the difficulty in providing a readily available active agent reservoir or conduit for injecting an active agent. The mechanical integrity of prior microneedles also suffers as their sizes become smaller and/or as they are made with readily biodegradable materials such as those preferred for use as solid solution perforators. Moreover, incorporating the prior art microneedles and arrays on an applicator device that can be easily used by any individual multiple times, and readily provide an active agent for multiple uses, is likely to be very cumbersome and expensive.

Moreover the FMA microdevice feature described herein has been shown to be effective for enhancing delivery of a variety of active agents, for example, as described in U.S. application publication Nos. 2008/0051695 and 2008/0214987. Also, for example, it has been established that FMA-enhanced delivery of lidocaine effectively manages pain as indicated in U.S. application publication No. 2007/060867, and as reported for a large clinical trial in Li et al., "Microneedle Pretreatment Improves Efficacy of Cutaneous Topical Anesthesia", *Am. J. Emergency Med.*, 28:130-134 (2010).

Accordingly, there remains a continuing need for an improved low cost, easy to use, multi-use, disposable percutaneous delivery device applicator with active agent for effective through the skin delivery of the active agent in a controlled manner.

SUMMARY OF THE INVENTION

In one embodiment, the present subject matter provides an applicator having a first region comprising a microdevice for perforating the skin and a second region comprising an active agent to be applied to the area of skin being perforated. An applicator of the present subject matter is disclosed having a microdevice for perforating the skin at a first region and an active agent for application to the skin stored in a first chamber at a second region. The microdevice component can comprise a plurality of high-aspect-ratio microneedles, microneedle arrays, microblades, microblade arrays, microknives, microknife arrays, or combinations thereof. In some embodiments, the microdevice is also called a Functional MicroArray (FMA).

The microdevice portion of the applicator is useful for perforating the stratum corneum layer, the outer layer of skin, without significant pain or discomfort to a patient. The microdevice is designed to permit percutaneous delivery of substances across the stratum corneum layer, the outer layer of skin, that is about 4-30 micron thick. The microdevice is designed so that it generally does not penetrate to the depth of sensory nerves that detect pain or discomfort in the skin. In some embodiments, the length of the microdevice is less than 150 μm. In some embodiments, the surface area of the microdevice ranges from 1 mm$^2$ to 2500 mm$^2$. In some embodiments, the density of microneedles, microblades, or microknives on the microdevice ranges from 20 per cm$^2$ to 20,000 per cm$^2$ The active agent stored in the applicator is applied to the area of skin being perforated by the microdevice. In many embodiments, the active agent is applied after the skin is perforated by the microdevice. In other embodiments, the active agent is applied to the area of skin being perforated before the skin is perforated by the microdevice.

It is therefore the primary object of the present subject matter to provide an applicator that provides in a single unit the features for performing a two-step method for efficient and efficacious delivery of drug compounds, vaccines and active cosmetic substances through the skin. The first step is the application of the microdevice on the applicator to the skin to generate a multiplicity of microchannels in the stratum corneum layer. The length of the microdevice's microneedles, microblades, and/or microknives is such that penetration depth does not reach the dermis layer to cause any pain or discomfort. This delivery is called intraepidermal delivery that is difference from traditional transdermal drug delivery and needle injections. The second step is to immediately remove the microdevice and apply one or more active substances to the area of skin perforated by the microdevice. The active substance(s) are stored in the applicator in a reservoir and applied directly from the applicator to the area of skin perforated by the microdevice, In another embodiment, an occlusive layer is applied over the active agent that has been applied to the perforated area of skin. In this regard, disclosed herein is an applicator for providing a safe, painless, and convenient method for percutaneous delivery of substances such as drugs, vaccines, and cosmetic compounds.

The applicator may optionally include one or more indicator features, or signals, for verifying compliance with predetermined methods of using the applicator, such as, for example, a light, sound, and/or vibration to indicate that the microdevice has been applied to the skin with the recommended amount of force for perforating the outer layer of skin. Non-limiting examples of indicator features, or signals, useful in this regard include a light signal, a sound signal, a vibration signal, a recorded counter signal, an electrically transmitted signal, an RF transmitted signal and combinations thereof In another embodiment, the present applicator can also use one or more indicator features or signals to indicate that the microdevice has been applied to the skin and has stayed on the skin for a pre-determined period of time. In a further embodiment, the present applicator can have a circuit to count how many times the applicator has been applied to the skin, wherein the one or more indicator features or signals can optionally change when a pre-determined number of applications is reached.

The applicator can be useful for providing an enhanced percutaneous delivery of an active agent, with minimal discomfort, for therapeutic or cosmetic treatment, such as, for example, topical treatment for acne, or other skin disorders, acne marks, hypigmentation, wrinkles, blemishes, etc. The applicator can also be useful for providing improved systemic or localized delivery of an active agent, such as, for example, lidocaine, salicylic acid, benzoyl peroxide, azeleic acid and its derivatives, L-carnitine, insulin, botulinum toxin, vitamin C and its derivatives, arbutin, niacinamide etc.

According, in another embodiment, the present subject matter relates to an applicator with at least one built-in non-verbal instructional device comprising:

a hollow body structure having a first end and a second end, and having an exterior surface and an interior surface;

said first end of said body structure having at least one built-in non-verbal instructional device to elicit correct behavior, rectify incorrect behavior and improve user compliance by producing instructional signals signifying one or more of the number of applications, the force of each application to validate each application, and the duration of each application;

said second end of said body structure containing at least one element selected from the group consisting of at least one opening to allow dispensing of an active agent that can treat certain diseases; at least one opening to allow dispensing of pigments or inks to temporarily change the appearance of skin; a connector that attaches to a personal communication device, personal entertainment device, writing device, knife, scissors, clump, pen sharpener, key chain, magnetic bar, cartoon head, decoration object or a toy; and a solid end without any opening.

In a further embodiment, the present subject matter relates to an applicator with at least one built-in non-verbal instructional device comprising:

a hollow body structure having a first end and a second end, and having an exterior surface and an interior surface;

said first end of said body structure comprising a microdevice for perforating only the skin's stratum corneum layer for intraepidermal delivery of active agents and at least one built-in non-verbal instructional device to elicit correct behavior, rectify incorrect behavior and improve user compliance by producing instructional signals signifying one or more of the number of applications, the force of each application to validate each application, and the duration of each application;

said second end of said body structure containing at least one element selected from the group consisting of at least one opening to allow dispensing of an active agent that can treat certain diseases; at least one opening to allow dispensing of pigments or inks to temporarily change the appearance of skin; a connector that attaches to a personal communication device, personal entertainment device, writing device, knife, scissors, clump, pen sharpener, key chain, magnetic bar, cartoon head, decoration object or a toy; and a solid end without any opening.

In a still further embodiment, the present subject matter relates to an applicator with at least one built-in non-verbal instructional device comprising a hollow body structure having a first end and a second end, and having an exterior surface and an interior surface;

said first end of said body structure comprising a microdevice for perforating only the skin's stratum corneum layer for intraepidermal delivery of active agents and at least one built-in non-verbal instructional device to elicit correct behavior, rectify incorrect behavior and improve user compliance by producing instructional signals signifying one or more of the number of applications, the force of each application to validate each application, and the duration of each application;

said second end of said body structure comprising an active agent reservoir comprising at least one active agent; and an active agent applicator portion that provides for release of the active agent from the active agent reservoir.

The subject matter described herein advantageously provides a disposable multi-use applicator having both a microdevice for painlessly perforating the outer layer of skin and a reservoir of active agent for providing a two-step method of enhanced delivery of a therapeutic or cosmetic active agent combined in a single convenient, inexpensive, and pocket portable unit. The ease of using a single applicator to perform the two-step method of enhanced delivery of a therapeutic or cosmetic active agent provides an added advantage for using the applicator described herein, and helps ensure patient compliance with treatment regimes requiring multiple repeated administrations over several days or weeks.

DETAILED DESCRIPTION OF THE INVENTION

Figure 1:
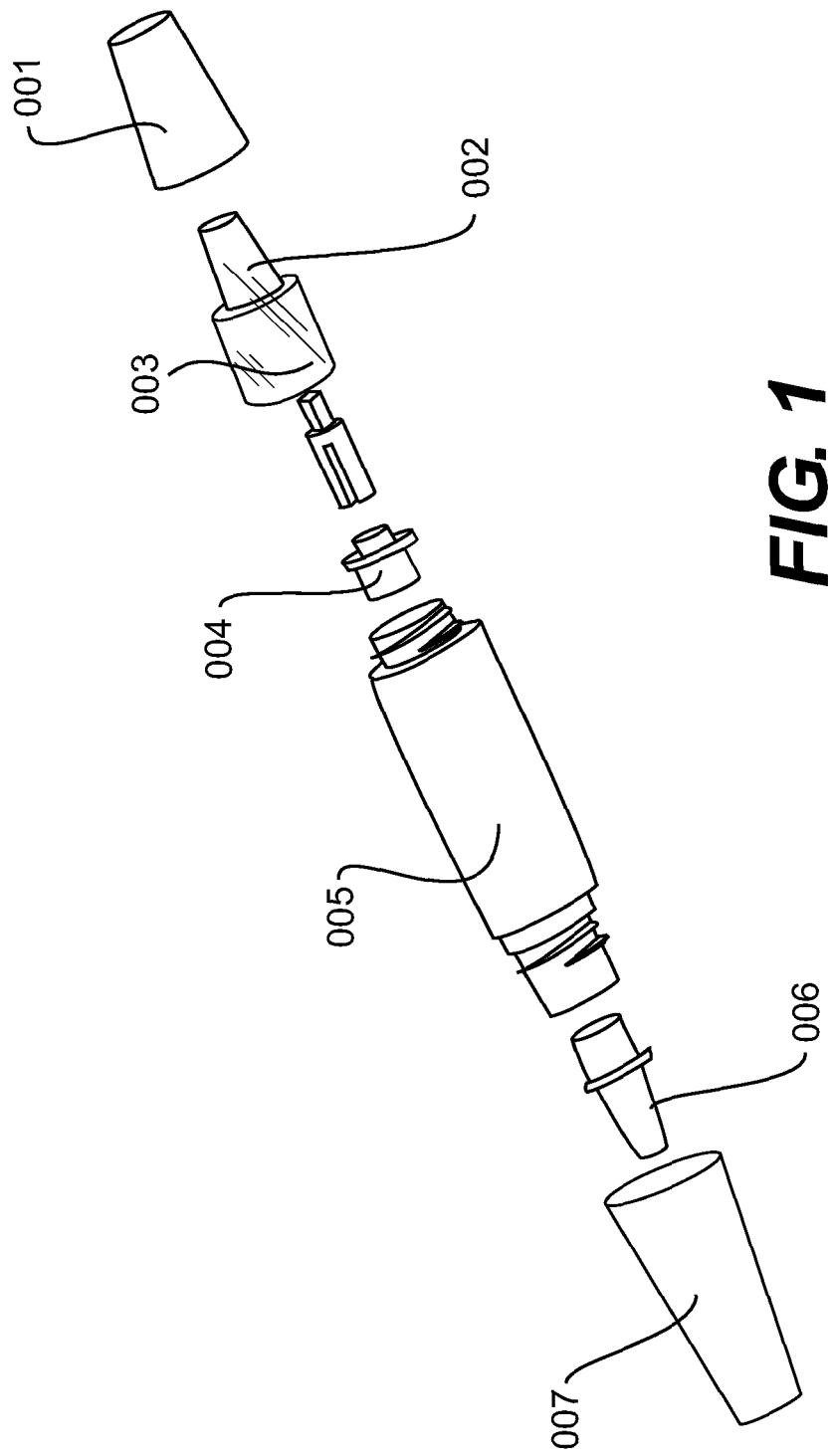
FIG. 1 is a schematic view of a first applicator embodiment showing an exploded view of all components. This embodiment includes an optional signal feature for verifying compliance with predetermined methods of using the applicator, such as, for example, a light, sound, and/or vibration to indicate that the microdevice has been applied to the skin with the recommended amount of force for perforating the outer layer of skin, the duration of application on the skin, the number of times the applicator has been activated etc.

The present subject matter provides an applicator having a first region comprising a microdevice for perforating the skin and a second region comprising an active agent to be applied to the area of skin being perforated. The microdevice component can comprise a plurality of high-aspect-ratio microneedles, microneedle arrays, microblades, microblade arrays, microknives, microknife arrays, or combinations thereof. In some embodiments, the microdevice is also called a Functional MicroArray (FMA). The present subject matter also provides methods of using the applicator for percutaneous delivery of drugs, vaccines, diagnostic agents and cosmetic substances for treating, preventing, or ameliorating a medical or cosmetic condition of a mammal such as a human being.

The applicators described herein provide in a single unit features for performing a two-step method for efficient and efficacious delivery of drug compounds, vaccines and active cosmetic substances through the skin. The first step is the application of the microdevice on the applicator to the skin to generate a multiplicity of microchannels in the stratum corneum layer. The length of the microdevice's microneedles, microblades, and/or microknives is such that penetration depth does not reach the dermis layer to cause any pain or discomfort. This delivery is called intraepidermal delivery that is difference from traditional transdermal drug delivery and needle injections. Accordingly, for intraepidermal drug delivery (IED) as described herein, it is important to use a microdevice or FMA having a length of less than 150 μm so as not to penetrate to the depth of sensory nerves that detect pain or discomfort in the skin.

The second step is to immediately remove the microdevice and apply one or more active substances to the area of skin perforated by the microdevice. The active substance(s) are stored in the applicator in a reservoir and applied directly from the applicator to the area of skin perforated by the microdevice, In another embodiment, an occlusive layer is applied over the active agent that has been applied to the perforated area of skin. In this regard, disclosed herein is an applicator for providing a safe, painless, and convenient method for percutaneous delivery of substances such as drugs, vaccines, and cosmetic compounds.

Skin Structure

Skin has a biological barrier called stratum corneum in its outer layer. This layer of about 20 microns thick prevents most of the molecules from penetrating through the skin. The layer below the stratum corneum is called viable epidermis. Epidermis is between 50 to 100 micron thick. The viable epidermis layer has no blood vessels and the molecules in this layer can be transported to and from the dermis, a layer under the viable epidermis, which is between 1 to 3 mm thick. There are blood vessels, lymphatics and nerves in the dermis layer. In preferred embodiments, the microdevice has microneedles, microblades, and/or microknives having a length that will perforate the stratum corneum and terminate in the epidermis layer, thus not reaching the dermis layer. To date, a skin patch is only able to deliver drug molecules of less than 500 Da. In addition, these small molecules are typically limited to hydrophobic drugs.

Requirement of Delivery of Drugs, Vaccines and Cosmetic Substances

Successful percutaneous delivery of therapeutic drugs, vaccines and cosmetic substances needs a way to transport molecules, especially large molecules, through the skin barrier, i.e., the stratum corneum. The substance can be delivered into the skin in any form acceptable to pharmaceutical requirements, but a gel formulation is preferred to achieve controlled release of active ingredients. Other topical delivery formulations, such as lotions, creams, ointments, solutions, foams, etc., can be used as well.

The microdevice described herein can be used for effective percutaneous delivery of an agent. The microdevice can be a microdevice array comprising a plurality of microstructures formed of a metallic, semi-conductor, glass, ceramic, or polymeric material. In some embodiments, the microdevice can be one or more microneedles, microknives, or microblades. In some embodiments, the microdevice comprises microstructures having a nanoscale tip or edge and a microscale body.

"Aspect-ratio" is defined herein as the ratio of the depth or height of a structure to its lateral dimension. High-aspect-ratio microstructures typically have an aspect ratio higher than about 5:1 and they may be useful for a variety of purposes. In the current subject matter, the tip of the microneedle or the edge of the microblade and microknife needs to be sharp in order to lower the insertion force, while the body of the microdevice should be long enough to allow it to completely penetrate the stratum corneum. A typical size of the needle tip or width of the edge on microblades and microknives is smaller than 10 microns, preferably smaller than 5 microns and the height of the microdevices is higher than 20 microns, preferably higher than 50 microns. The aspect ratio of these microdevices, in a preferred embodiment of the current subject matter, is higher than 10:1 with the size of the tip and edge smaller than 5 microns and the height of microdevices higher than 50 microns. Microdevices of the present subject matter generally comprise high aspect ratio microneedles, microblades, or microknives for perforating the skin and thus facilitating delivery of an active agent through the resulting perforations in the skin.

In some embodiments, the microdevice in the applicator comprises microneedles, microblades, or microknives having a length ranging from 4 to 500 microns. In one embodiment, the microdevice in the applicator comprises microneedles, microblades, or microknives having a length ranging from 10 to 200 microns. In another embodiment, the microdevice in the applicator comprises microneedles, microblades, or microknives having a length ranging from 20 to 100 microns.

In another embodiment, the applicator described herein can have a volume of at least 0.1 cm$^3$. This minimum volume can be inclusive of any built-in non-verbal instructional devices or active agents contained therein. In a preferred embodiment, the applicator has a volume of 0.1 to 10 cm$^3$.

The Microneedles

Figure 6:
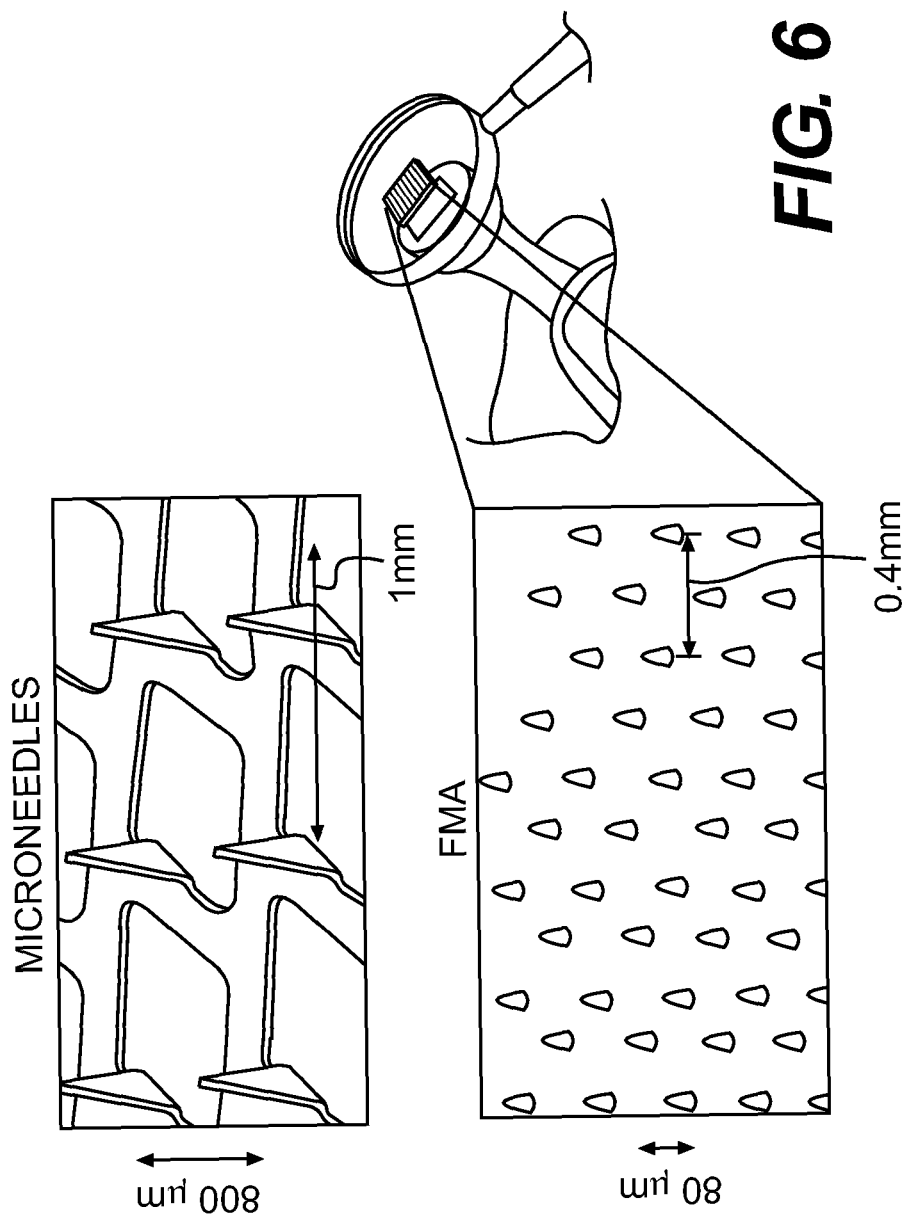
FIG. 6 shows scanning electron microscope micrographs of examples of two different microneedle arrays having different microneedle sizes and density of microneedles. These microneedle arrays are examples of those that may be found on an applicator described herein.

The microneedle devices disclosed herein can contain one or more microneedles. In some embodiments, the length of the microneedle is typically in the range of 20-500 microns, sufficient to pierce through the outer skin barrier layer and deliver molecules to viable epidermis or even deeper. In preferred embodiments, the microneedles have a length that does not reach into the dermis where blood vessels and nerves might be disturbed. The diameter of a single microneedle is typically in the range of 30-300 microns with a sharp tip of less than 10 microns to cause little discomfort to the patients while maintaining mechanical integrity. In one embodiment of the subject matter, the needle tip is less than 2 microns and the height of the needle shaft is about 100 microns. The aspect ratio is 50:1. In one embodiment, the angle of the tip is between 30 to 75 degrees, typically between 38-72 degree. FIG. 6 shows a micrograph of microneedle arrays fabricated by this method with a zoom in view of a single microneedle that has a base diameter of about 80 microns. In one embodiment of the current subject matter, the inner diameter of the needle tip is about 10 microns and the height of the needle is about 1200 microns to allow sufficient extraction of body fluids. The aspect ratio is preferably 120:1.

The Microblades and Microknives

The microblades and microknives disclosed herein can contain one or more blades or knives. The sharp edge of these devices is below 10 microns wide and the height of the body is more than 100 microns. In a preferred embodiment of the current subject matter, the edge is below 3 microns and the body height is about 150 microns. The skin contact area is about (0.003 mm×1 mm) for each microblade or microknife. The leading angle of the blade edge is between 30 to 75 degrees, preferably between 38-72 degrees.

Materials and Device Sterilization

The devices can be made of many different materials or their combinations, including metals, ceramics, polymers and glass. Examples of the materials are titanium, stainless steel, nickel, alloy of nickel-iron, silicon, silicon oxide, glass, polymethyl methacrylate (PMMA), polyaryletherketone, nylon, PET, poly(lactic acid), poly(glycolic acid) (PGA), poly(lactic-co-glycolic acid) (PLGA), polycarbonate, and polystyrene. It should have enough mechanical strength to penetrate skin without break and buckle while ensuring delivery of drugs, or collection of biological fluids. They can be sterilizable using established protocols (see, for example, moist heat, ethylene oxide or radiation sterilization as stated by ANSI/AAMI/ISO 11134:1993, ANSI/AAMI/ISO 11135:1994 and ANSI/AAMI/ISO 11137:1994).

The Microchannels

High-aspect-ratio microchannels can be embedded in microdevices to allow flexible manipulation of microfluidics and connect microneedles to other functional blocks such as drug reservoirs. Microchannels can be made of many different materials or their combinations, including metals, ceramics, polymers and glass.

Method of Use

The device described herein can be used for percutaneous delivery of an agent to treat, prevent, or ameliorate a body condition in need of treatment. The method generally includes treating a skin site of delivery with a microdevice described herein, and delivery of an agent to the body of a mammal (e.g., a user or patient).

In general, the applicator is used so that one or more active agents is applied to the area of skin being perforated either immediately before the area of skin is perforated by the microdevice, or immediately after the area of skin is perforated by the microdevice. In general, the applicator is used so that the microdevice is immediately removed from the skin after the microdevice perforates the skin. In some embodiments, the applicator can be used to apply the microdevice to the skin a multiple number of times during a single treatment. By applying the applicator more than once during a single treatment, the applicator may be used to perforate the skin over a larger surface area, or at multiple different locations on the patient.

In some embodiments, a second active agent can be applied to the area of skin being treated by the applicator. This second agent may be contained in a second active agent chamber in the applicator. In alternative embodiments, the second active agent is separate from the applicator and contained in a separate form apart from the applicator, such as a separate tube, vial, pad, patch etc.

The body condition can be a medical condition or a cosmetic condition. Representative medical conditions include, but are not limited to, AIDS, breast cancer, melanoma, liver cancer, lung cancer, blood cancer, pituitary tumors, other cancers, flu, infection, blood disease, cardiac disease, back pain, neck pain, body pain, general pain, arthritis, osteoporosis, headache, depression, smoke, alcoholic, overweight and obesity, menopause, facial hair growth, balding, polycystic ovary syndrome, need of inoculation, need of anesthetics and in particular dermal disease. Representative cosmetic conditions include, but are not limited to, skin aging, skin wrinkle, dark spot, skin discoloration, moisturizing, skin lightening, skin whitening, skin firming, skin lifting, acne, acne mark, acne scar, cellulite, wart, infection, irritation, dry skin and oily skin.

The applicators of this subject matter are designed as disposable devices, re-usable devices, and/or recyclable devices. In one embodiment, the applicators are disposable after one or more uses. In another embodiment, the applicator can be recycled by providing a new active agent and/or a new microdevice. The applicator may be sterilized before and/or after each use by using a sterilization method known in the art.

The applicators disclosed herein are effective in increasing the skin diffusion of molecules, especially therapeutic molecules with molecular weight higher than 500 Daltons and hydrophilic molecules to transport through the skin barrier. It has been found that the enhancement of percutaneous transport was also observed for small molecules with a molecular weight lower than 500 Daltons, as well as large molecules with a molecular weight higher than 500. Because the height of the microneedles and microblades is limited, it will not reach the nerve-rich dermis layer and cause any discomfort to the subject.

Active Agent

Active agents or active substances that can be delivered using the applicator are therapeutic agents and/or cosmetic agents. The phrase "therapeutic agent" is used herein to refer to active agents that can treat, prevent, and/or ameliorate a body condition or skin condition that needs treatment. The phrase "cosmetic agent" is used herein to refer to active agents that can treat, prevent, conceal, and/or ameliorate a cosmetic body condition or skin condition that needs treatment. A list of examples includes, but is not limited to: drugs, vaccines, peptides, proteins, genes, DNAs, nutraceuticals and cosmetics. The drugs can be administered topically and systemically. Examples of the drugs as active agents include, but are not limited to, antibiotics, hormones, steroids, anti-inflammatory drugs, protein drugs, DNA drugs whether natural or synthesized, such as benzoyl peroxide, azeleic acid and its derivatives, L-carnitine, botulinum toxin, koji acid, arbutin, niacinamide, Recombinant Erythropoietin (rhEPO), Taxol (R), Interferon-alpha-1b, Interferon beta, Interferon gamma, Emla(R), Fluorouracil, Lidocaine, Salicylic acid, Pureriran, eflornithine hydrochloride, spironolactone, flutamide, insulin, nanoparticle drugs, Epidural, recombinant human parathyroid hormone, growth hormone, thyroid, cortisol, estrogen, progesterone, and testosterone. Examples of vaccines active agents include, but are not limited to: vaccine against influenza (flu), diphtheria, tetanus, pertussis (DTaP), measles, mumps, rubella (MMR), hepatitis B, polio, haemophilus influenzae type b, chickenpox, tuberculosis, anthrax, yellow fever, rabies, AIDS, cancers, meningococcus, SARS and cholera. More examples of cosmetic substances as active agents include, but are not limited to: botulinum toxin type A, hyaluronic acid and its derivatives, acetyl hexapeptide-3, vitamin A, vitamin C and its derivatives, vitamin E, alpha-hydroxyacids, collagen and hormones. Diagnostic reagents are also included. Examples include, but are not limited to, quantum dots, functionalized nanoparticles, and magnetic particles for diagnostic purpose. In some embodiments, the active agent is combined with a cosmetic concealer which may conceal a skin blemish.

The dosage of the agent can vary according to the medical condition being treated. The effective amount of an agent that has been well established in the art can be publicly available. Such information can be obtained from the U.S. Food and Drug Administration (FDA), e.g., FDA website. For example, LidoDerm(R) info can be found in this link: http://www.fda.gov/medwaTCH/SAFETY/2006/Apr_PIs/Lidoderm_PI.pdf#search=%22lidoderm%20dosage%22.

In some embodiments, the agent is a pain relieving drug for neuropathic or nociceptive pain management. Such pain relieving drug includes, but is not limited to, Lidocaine; Prilocaine, Tetracaine, Ibuprofen; Acetaminophen; Capsaicin; EMLA(R); Tramadol (Ultram); Gabapentin, Tramadol hydrochloride, Corticosteroids, Sufentanil, Clonidine, Bupivacaine, Tricyclic antidepressants, opioid analgesics such as morphine, Hydromorphone, naloxone (Narcan), Talwin, Nubain, Stadol, Fentanyl, Meperidine, Hydrocodone, Codeine, Oxycodone; non-selective NSAIDs such as Celecoxib (Celebrex), rofecoxib (Vioxx), valdecoxib (Bextra); or combinations thereof. In some embodiments, the pain relieving drug described herein can specifically exclude any of the drug/agents listed herein.

In some embodiments, the active agent can be muscle relaxants, which include, but are but are not limited to, Benzodiazepines; Methocarbamol; Carisoprodol; Chlorzoxazone; Metaxalone; Cyclobenzaprine, or combinations thereof. In some embodiments, the muscle relaxants described herein can specifically exclude any of the drug/agents listed herein.

Drug Delivery

In one aspect, the present subject matter provides an applicator for delivery of the therapeutic active agent as defined above across the skin barrier, or stratum corneum layer. Once the substances pass the stratum corneum, there is less resistance for the substances to diffuse into the subsequent layers of the skin: epidermis and dermis. The substances will be absorbed by microvessels and lymphatics in the dermis layer and can be delivered to the entire human body. Applicators disclosed in the current subject matter can enhance skin penetration of molecules of a molecular weight lower than 500 Dalton. Applicators can also enable through the skin transport of large molecules of a molecular weight higher than 500 Dalton, as exemplified by Bovine Serum Albumin at 66,000 Dalton, Botulinum Toxin Type A at 150,000 Dalton, and the Interferon-Alpha-lb at 17,000 Dalton.

The active agent stored on the applicator is applied to the area of skin being perforated by the microdevice. In many embodiments, the active agent is applied after the skin is perforated by the microdevice. In other embodiments, the active agent is applied to the area of skin being perforated before the skin is perforated by the microdevice.

Topical Delivery of Cosmetic Substances

It is known to one in the art that certain substances have specific functions as cosmetics. For example, Botulinum Toxin Type A is a toxin that blocks neuromuscular transmission when it is injected in small amounts (e.g., 10 units per 0.1 ml injection volume) into specific muscles to treat and reduce wrinkles on the face. The maximum dosage recommended as a single injection for any one muscle at any spot is 25 units. If overdosed or the injection is incorrectly performed, the patient can be left with an immobile face or droopy eyelids until the effect of the injection wears off. Possible side effects include numbness, swelling and headaches. Administered through applicators disclosed in the current subject matter, it is possible to provide a controlled release of Botulinum Toxin Type A and keep an optimal local concentration to achieve the best result while minimize the side effects. In one embodiment of this subject matter, botulinum toxin type A is applied to the skin pre-treated with the applicator described herein. A significant increase in through the skin penetration of botulinum toxin type A has been observed. No through the skin transport was observed without application of applicators. More examples were provided in the above “active agents” section.

It is also evident that through the skin transport on applicator treated skin has less dependency on molecular weight. Using the applicator described herein, practically any cosmetic substances can be delivered. Local concentration can be adjusted through loading and formulation for controlled release. In one embodiment of this subject matter, one can deliver hyaluronic acid gel through diffusion enhanced by applicators. Hyaluronic acid is a substance that exists naturally in the body. A major important function of hyaluronic acid is to carry and bind water molecules. Stabilized non-animal hyaluronic acid does not contain animal protein and does not require a skin test prior to treatment. It is thus a preferred embodiment of this subject matter to use applicators to delivery locally stabilized non-animal hyaluronic acid to treat wrinkles and facial lines.

In a further embodiment of this subject matter, one can locally delivery collagen by microneedles, e.g., for allergic skin test and controlled release of collagen into the skin.

Another embodiment of this subject matter is to provide for local delivery of acetyl hexapeptide-3. This molecule is a non-toxic, non-irritant compound that modulates the excessive stimulation of the facial muscles, relaxing facial tension and it can reduce and prevent the formation of new wrinkles due to over-stimulation of facial muscles. More examples include but are not limited to: vitamin A, vitamin C and its derivatives, vitamin E, alpha-hydroxyacids, hormones, or combinations thereof.

Delivery of Vaccines

In some embodiments, the applicator provided herein can be used for topical delivery of vaccines below the stratum corneum layer. The type of vaccines includes conventional vaccines as well as protein, peptide, DNA vaccines and the like as previously described. Vaccination can be performed by treating a skin side with the applicator and then delivering a vaccine composition to a user.

Pain Management

In some embodiments, the applicator described herein can be used for pain management. The applicator can be used to facilitate percutaneous delivery of a pain relieving agent or a combination of them so as to treat, reduce or prevent pain. In some embodiments, a skin side can be treated with the applicator and then a pain relieving agent or drug composition can be delivered percutaneously to a user.

The pain relieving agent can be any pain relieving agent approved by the FDA or used in medical practice elsewhere in the world. In some embodiments, the pain relieving drug can be, but is not limited to, NSAIDs, COX-2 inhibitors, steroids, muscle relaxants. Specifically, such as Lidocaine; Prilocaine, Tetracaine, Ibuprofen; Acetaminophen; Capsaicin; EMLA (R); Tramadol (Ultram); Gabapentin, Tramadol hydrochloride, Corticosteroids, Sufentanil, Clonidine, Bupivacaine, Tricyclic antidepressants, opioid analgesics such as morphine, Hydromorphone, naloxone (Narcan), Talwin, Nubain, Stadol, Fentanyl, Meperidine, Hydrocodone, Codeine, Oxycodone; non-selective NSAIDs such as Celecoxib (Celebrex), rofecoxib (Vioxx), valdecoxib (Bextra); or combinations thereof. In some embodiments, the pain relieving drug described herein can specifically exclude any of the drug/agents listed herein.

The pain management can be carried out according to a management regime prescribed by a treating doctor. For example, in some embodiments, the pain management is chronic or acute pain management. The pain management regime can be but is not limited to, low back pain, postherpetic neuralgia, cancer pain, diabetic neuropathy, phantom limb pain, spinal stenosis/sciatica, spinal mets, HIV pain, pain caused by invasive medical procedures such as needle injection, and cannulation.

Controlled Release

The applicators need to deliver drug molecules through the skin at a rate that is sufficient to maintain a therapeutic useful concentration in plasma. The size and density of the microneedles, microblades, and/or microknives on the microdevice can be adjusted to meet the delivery requirement. In a preferred embodiment, the active agent is present in the active agent chamber and applied to the area of skin being perforated after the microdevice is applied to the skin and immediately removed. In some embodiments, the active agent is formulated with one or more physiologically acceptable carriers. In one embodiment, the active agent formulation may comprise one or more rheology modifiers, surface active agents, stabilizers, rehydration agents, and combinations thereof. In other embodiments, hydrogels of the active agent can be prepared using carbomer polymers, including, for example, CP940, CP974, CP980 and CP1342. The special active agent formulation can control the diffusion rate of the active drug molecule and regulate the drug release rate.

The Integrated Indicator Signal Device

The applicator may optionally include one or more integrated indicator signal device(s), or built-in non-verbal instructional device(s). In this regard, a built-in non-verbal instructions device as used herein can refer to a battery powered device with at least one signal emitting or producing element that can be switched on and off according to application specifications. Such devices can produce or provide various signals for verifying compliance with predetermined methods of using the applicator, such as, for example, a light, sound, vibration, RF transmitted signal, recorded counter signal, and/or an electric transmitted signal, or other indicator feature or signal described herein, to indicate that the microdevice has been applied to the skin with the recommended amount of force for perforating the outer layer of skin. In one embodiment, the microdevice is located on an actuator arm in the applicator and is applied to the area of skin being perforated. As force is applied to the surface of the microdevice at the skin the microdevice and actuator arm is pushed toward an integrated signal device. When the actuator arm applies sufficient force to the signal device, a force-sensitive switch in the signal device is activated which then triggers a signal. The signal may be any signal that can be detected by the user or by another observer. For example, the signal may be emission of light, sound, vibration, or an electrical signal to a second signaling device, data recorder, user, or observer. The integrated signal device can have a built-in circuit to record the force being applied, the duration of application, and/or the number of accumulated applications to monitor for the expected expiration of the device. The signal of light, sound, and/or vibration can be different based on wavelength, frequency, vibration patterns, a combination thereof, and the like.

In a preferred embodiment, the amount of force required to activate the signal device will be an amount of force sufficient for the microdevice to perforate the stratum corneum. In some embodiments, the amount of force required to activate the signal device can be adjusted by adjusting the signal device switch mechanism and/or actuator arm action. The amount of force required might be adjusted in order to provide more careful and delicate application to softer skin areas (such as, for example, around the eyes) or patients with more sensitive skin (such as, for example, in children or persons with hyper-sensitive skin). In a preferred embodiment, the signal device is switched off when the applicator is removed from the skin as the required force is removed. In some embodiments, the signal is a light signal, a sound signal, a vibration signal, or a combination thereof.

In another embodiment, the signal device is connected to a timer and an event counter to record the duration of time and the number of times the applicator has been applied. In other embodiments, the counter may optionally have a second signal device which activates when a pre-specified number of applicator uses has been reached. For example, after a number of pre-specified uses the counter signal might indicate that the applicator should be cleaned, replaced, or discarded. Such a counter may then help ensure the device is in optimal condition for providing the indicated treatment.

Methods for Microdevice Fabrication

The microdevices may be fabricated using MEMS microfabrication technology. The typical fabrication process involved lithography, wet etch and dry etch, thin film deposition and growth, electroplating, as well as injection molding and hot embossing. One example of fabrication method was to use Bosch process that allowed deep Si etch (www.oxford-plasma.de/process/sibo-1.htm). It formed microdevices suitable either as device body or mold for further processing and, for example, is described in previous published patent applications. Yet another fabrication method can use HF solution to electrochemically form porous Si structures (www.techfak.uni-kiel.de/matwis/amat/poren/ps.html). Metals can be used for the fabrication of microdevice through a maskless process called electropolishing starting from a structure fabricated by traditional machining methods such as cutting, electro-discharge machining, milling, grinding, polishing and drilling (www.najet.com and www.fischion.com/product support/model 110 application notes.asp). Use of any single method herein or a combination of these methods as further disclosed in the examples below led to the form of desired microdevice disclosed in the current subject matter.

Packaging

In a further embodiment of the present subject matter, the applicator described herein can be suitably packaged to permit easy one-press removal of the applicator from the package. In this regard, the present subject matter can relate to a package for an applicator, comprising: an outer container and an inner packaging material, wherein the inner packaging material comprises an indent shaped to contain an applicator as described herein and a further depression underneath the indent shaped to contain the applicator.

According to this embodiment, the applicator can be placed in an inner packaging material in a package with one end over a depression. Preferably, the applicator is placed in an indent in the inner packaging material shaped to hold the applicator. The depth of the depression can vary from 2 mm to 50 mm. In another embodiment, the depression can optionally contain bumps of 1 mm to 30 mm therein. When the end of the applicator over the depression is pressed into the depression, the other end of the applicator will move up, making it easy to take the applicator out from the package. The package of the present subject matter preferably comprises an outer container. The outer container can be any container suitable for holding the inner packaging material and the applicator therein. One non-limiting example of a suitable outer container is a carton. The carton may be made of any suitable material that provides the structural support for holding the first product container and the second product container. Materials useful as the carton include, without limitation, cardboard, paper, metal and plastic. In an alternative embodiment, the outer container comprises shrink-wrap.

The outer container of the present packaging may also contain an item selected from the group consisting of a single bar code, a single new drug code, and a single universal product code.

In a further embodiment, the inner packaging material may be any material firm enough to hold the applicator in place, yet able to absorb any vibrations to ensure the safety and stability of the applicator (i.e., to ensure that the applicator does not break before it is ready for use.) Non-limiting examples of preferred inner packaging materials in this regard include a shaped foam or carton.

EXAMPLES

Example 1

FIG. 1 is a schematic view of a first applicator embodiment showing an exploded view of all components. This embodiment includes an optional signal feature for verifying compliance with predetermined methods of using the applicator, such as, for example, a light, sound, and/or vibration to indicate that the microdevice has been applied to the skin with the recommended amount of force for perforating the outer layer of skin.

| Component | Name & Function |
|---|---|
| 001 | Outer Cap, FMA microdevice end |
| 002 | FMA protective sleeve |
| 003 | FMA microdevice and actuator arm |
| 004 | Integrated Signal Device |
| 005 | Active Agent Reservoir and Body |
| 006 | Applicator tip nozzle |
| 007 | Outer Cap, gel agent end |

The Active Agent Reservoir and Body 005 has a soft wall. When pressed, gel/lotion/cream contained therein can be squeezed out from the Applicator tip nozzle 006 to an area of skin pretreated with the FMA microdevice and actuator arm 003. The Integrated Signal Device 004 has one ore more of timer, force switch, counter to signal the force applied to skin, time duration of each application and the total accumulated number of applications.

Figure 2A:
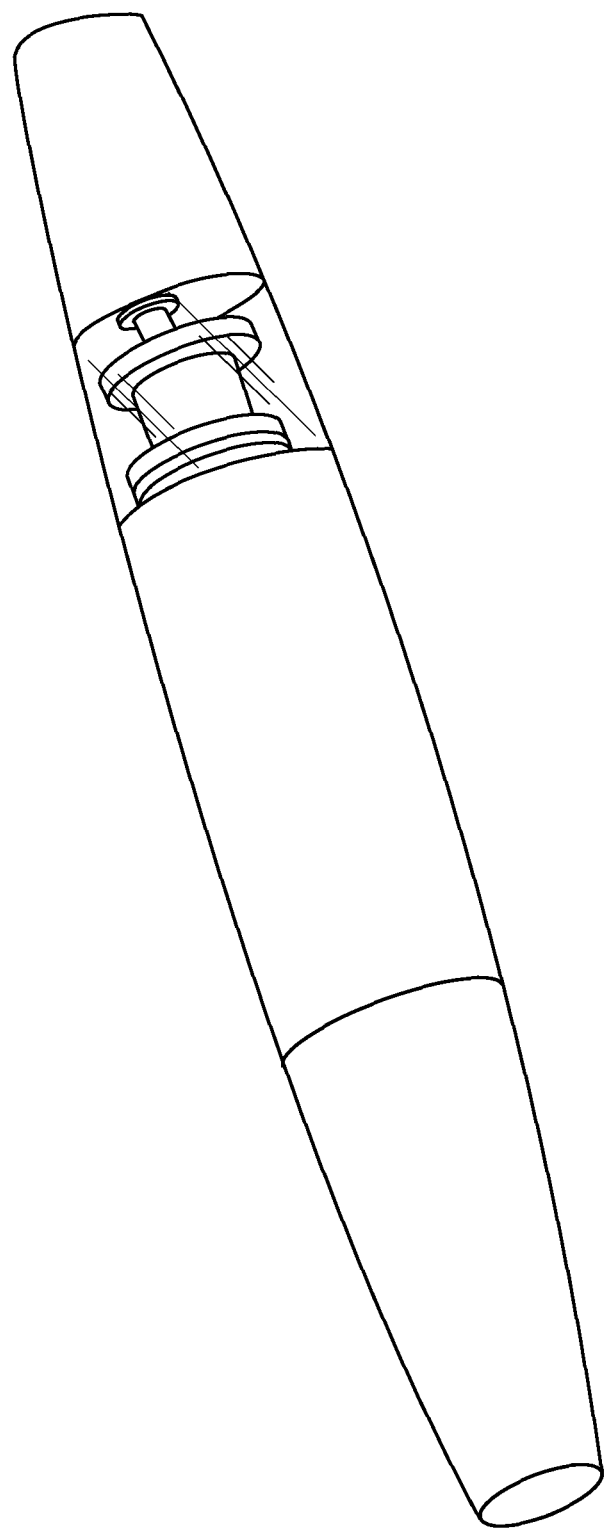
FIG. 2 shows schematic views of the first applicator embodiment having a microdevice for painlessly perforating the outer layer of skin and a reservoir of active agent.
Figure 2B:
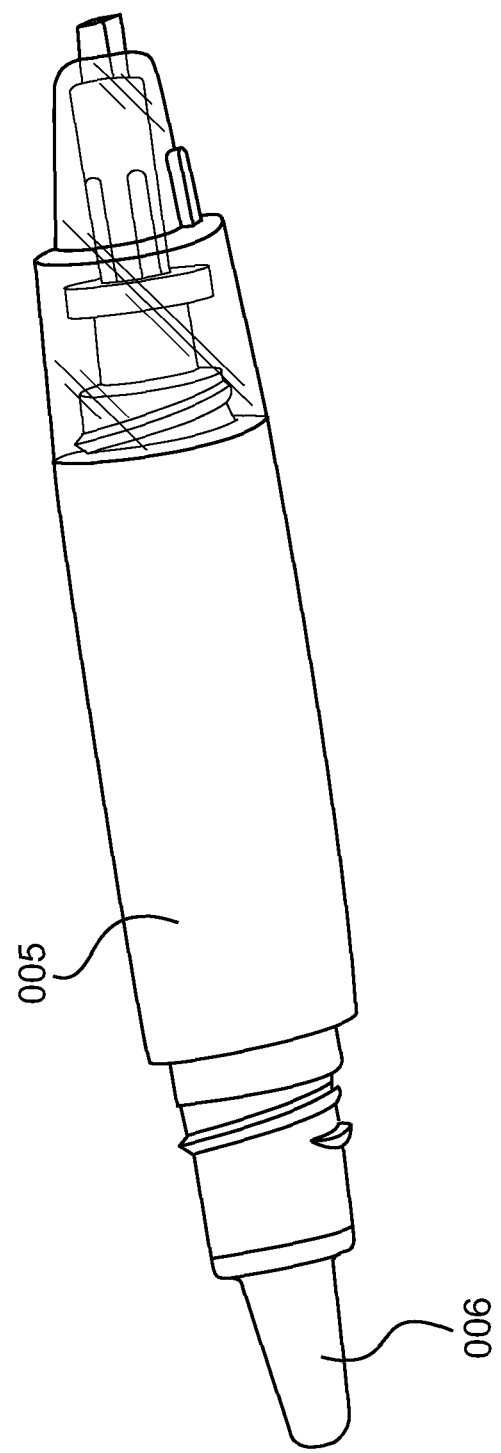

FIG. 2 shows schematic views of the first applicator embodiment having a microdevice for painlessly perforating the outer layer of skin and a reservoir of active agent.

Figure 3A:
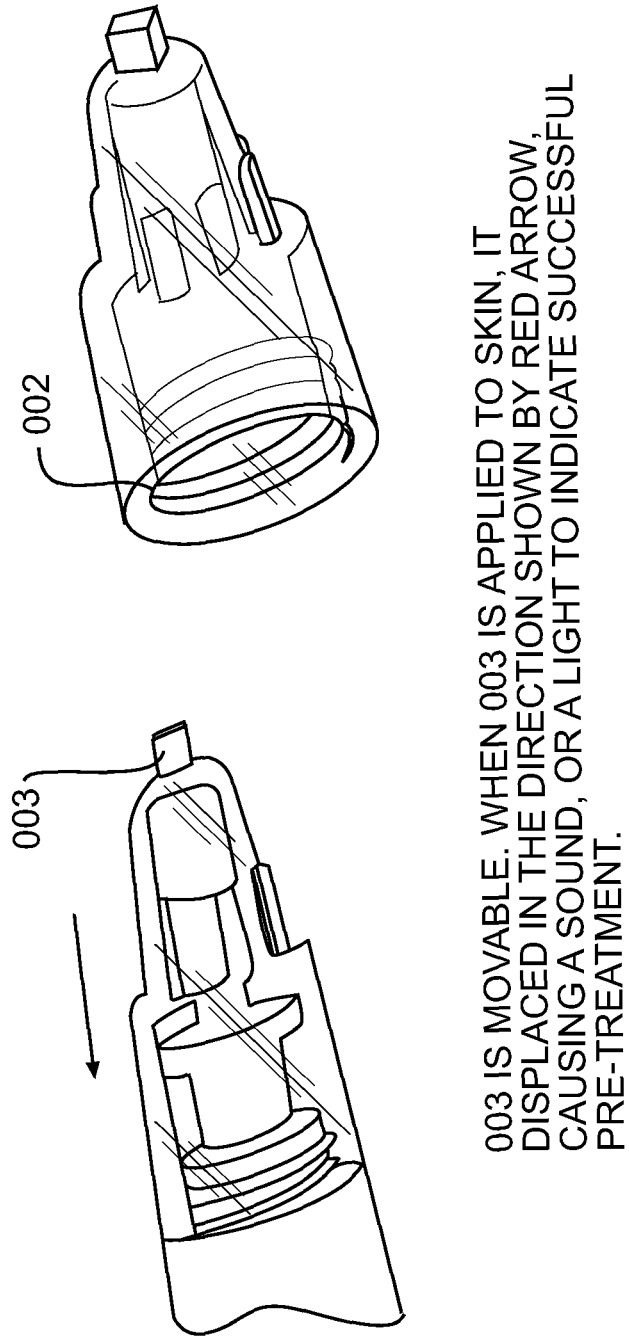
FIG. 3 shows a schematic view of the first applicator embodiment wherein the FMA microdevice moves the actuator arm when contacting the skin. The actuator arm thereby contacts the pressure sensitive signal device which generates a signal when sufficient force is applied when contacting the skin with the microdevice to perforate the skin.
Figure 3B:
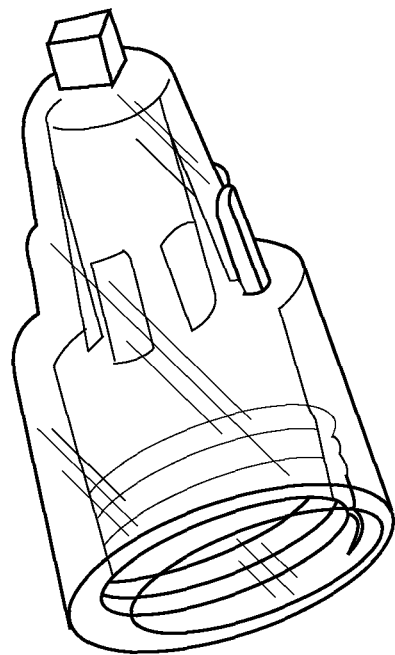
Figure 3B:
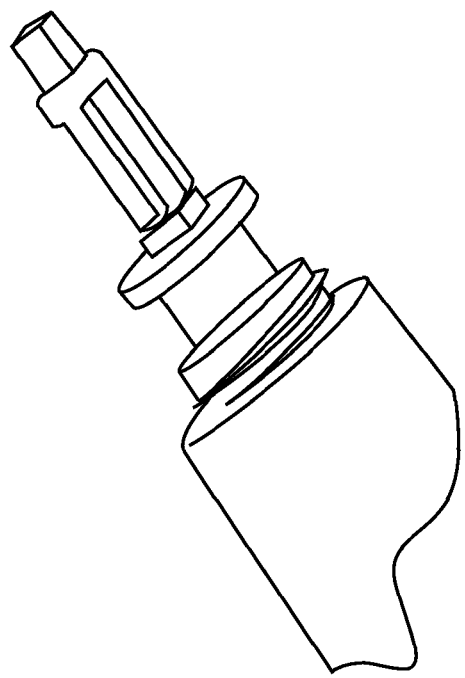

FIG. 3 shows a schematic view of the first applicator embodiment wherein the FMA microdevice moves the actuator arm when contacting the skin. The actuator arm thereby contacts the pressure sensitive signal device which generates a signal when sufficient force is applied when contacting the skin with the microdevice to perforate the skin.

Example 2

Figure 4:
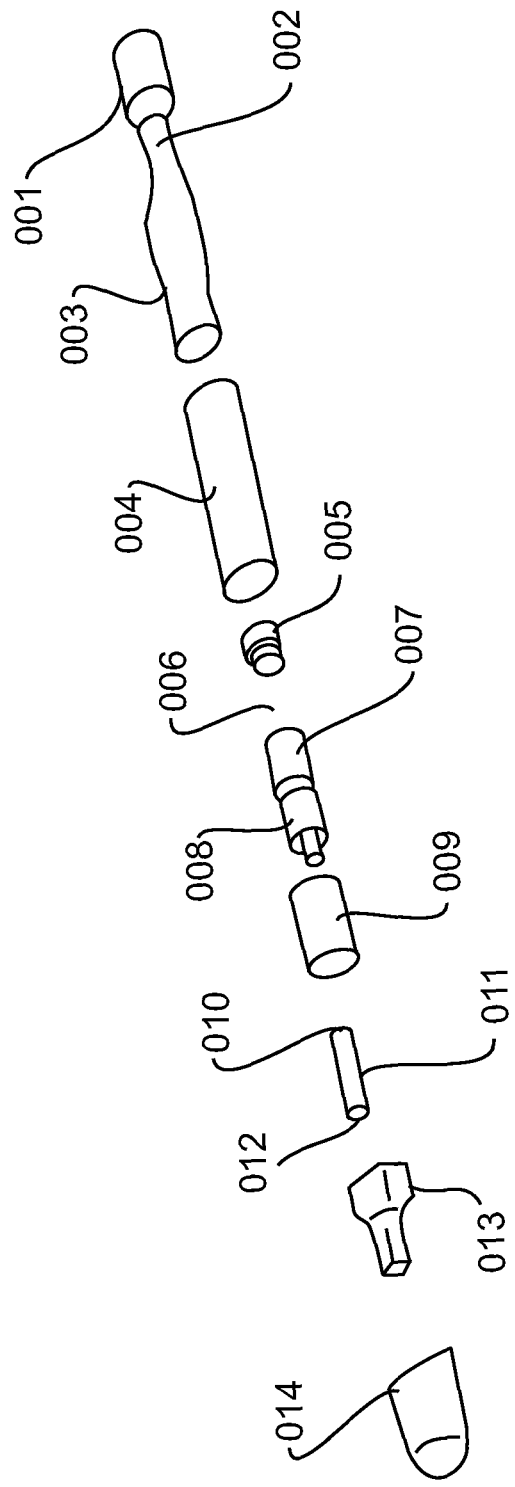
FIG. 4 is a schematic view of a second applicator embodiment showing an exploded view of all components. This embodiment includes an optional signal feature for verifying compliance with predetermined methods of using the applicator, such as, for example, a light, sound, and/or vibration to indicate that the microdevice has been applied to the skin with the recommended amount of force for perforating the outer layer of skin, the duration of application on the skin, the number of times the applicator has been activated etc.
Figure 5A:
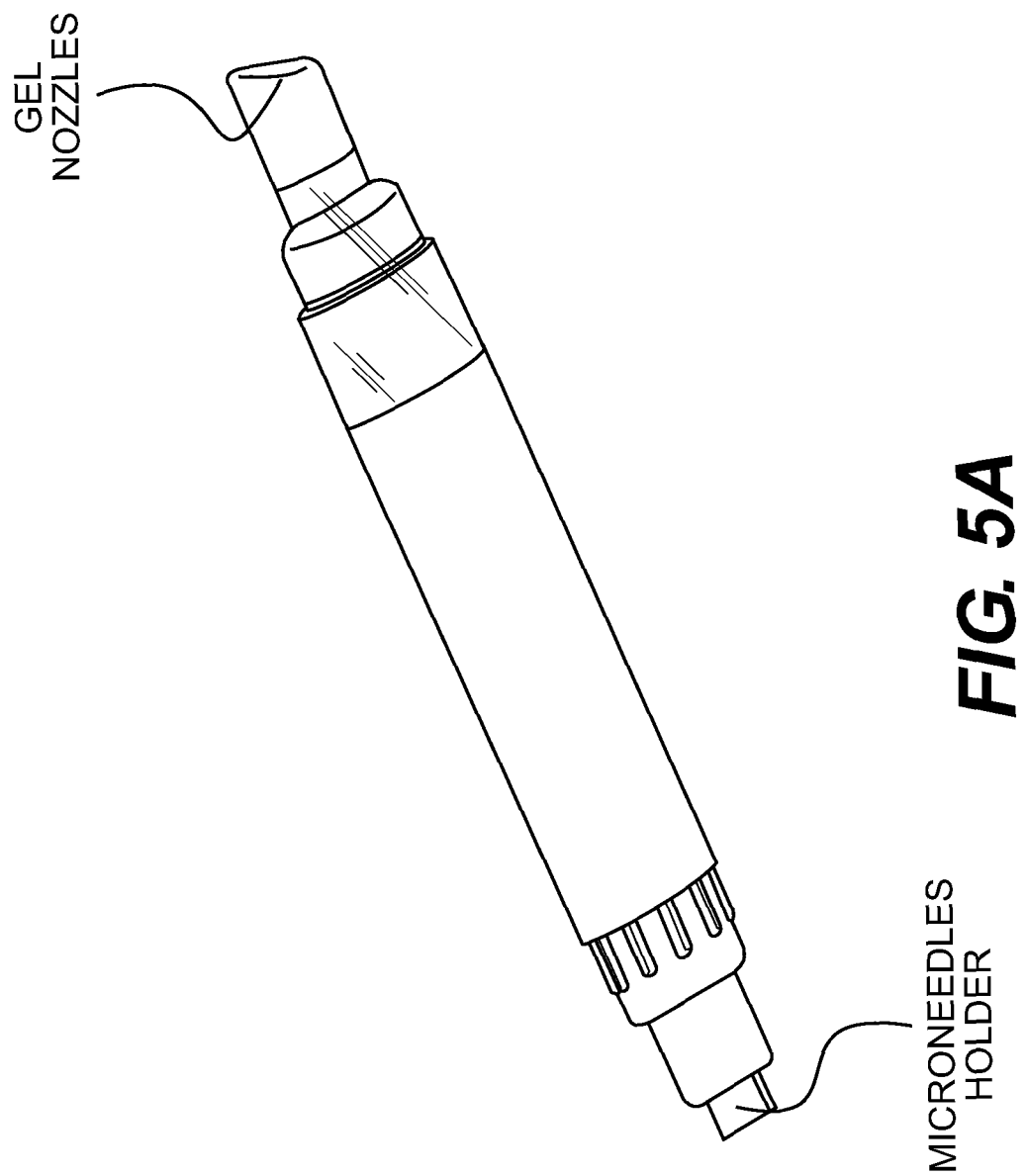
FIG. 5 shows schematic views of the second applicator embodiment having a microdevice for painlessly perforating the outer layer of skin and a reservoir of active agent.
Figure 5B:
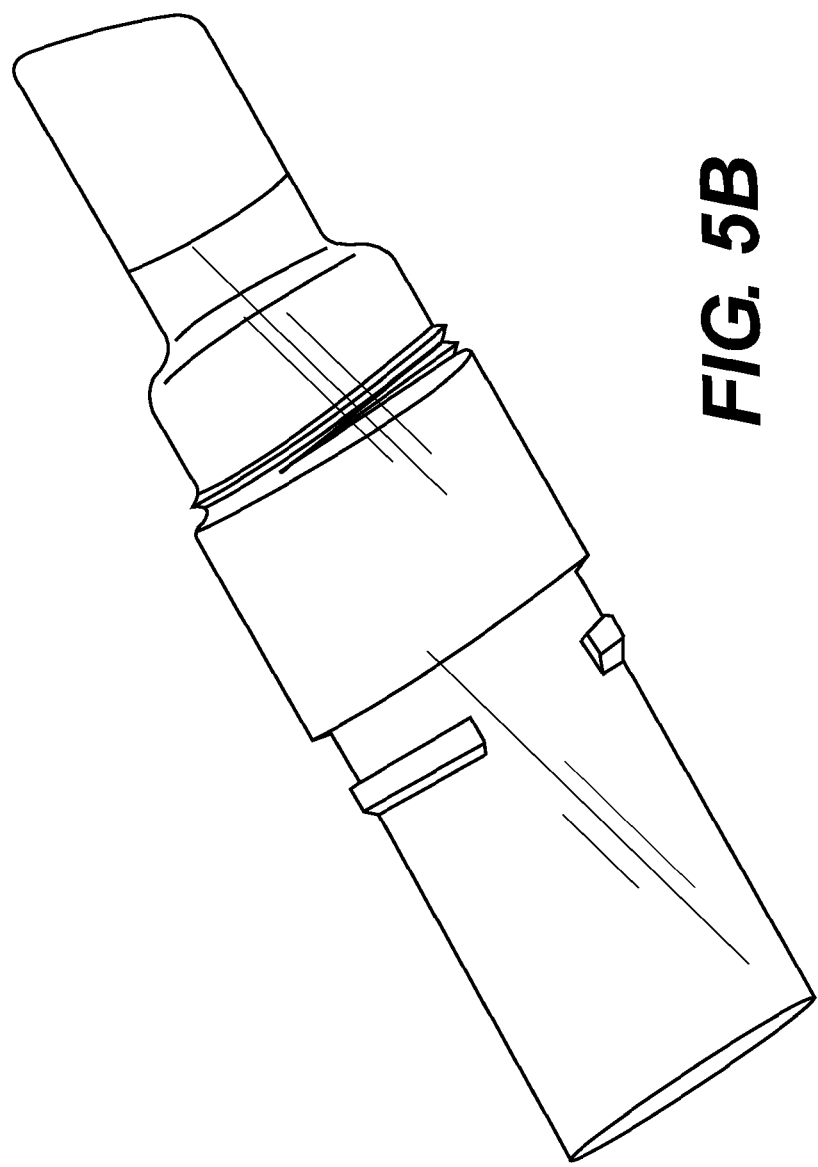
Figure 5C:
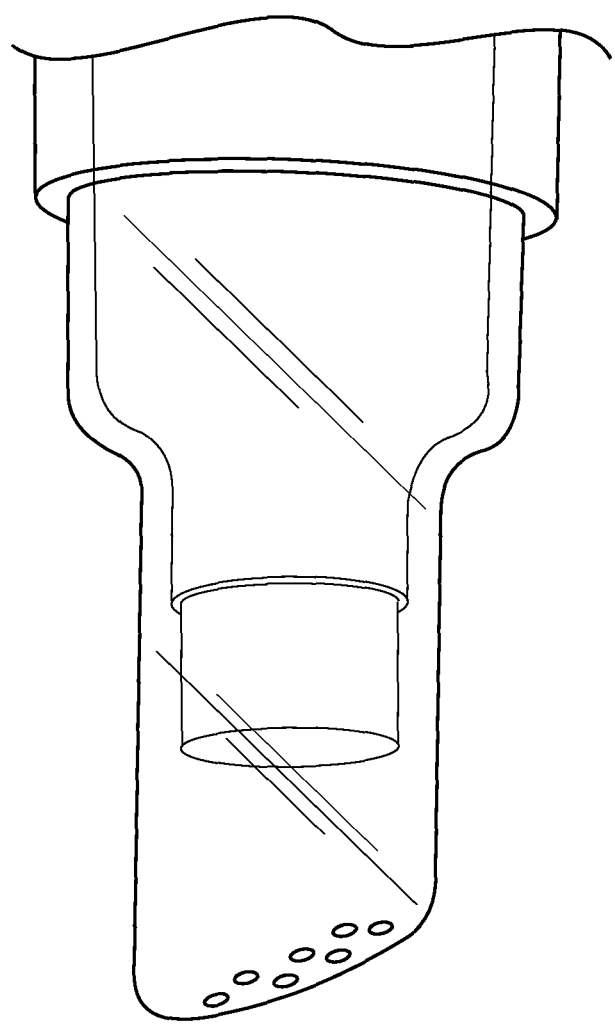
Figure 5D:
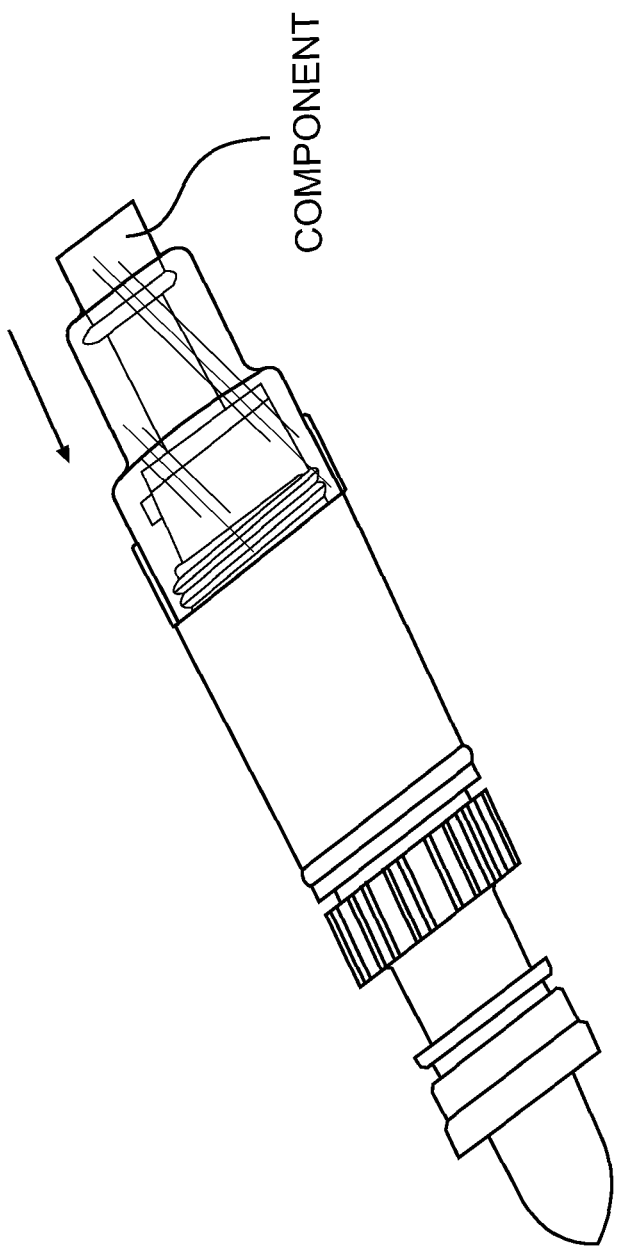
Figure 5E:
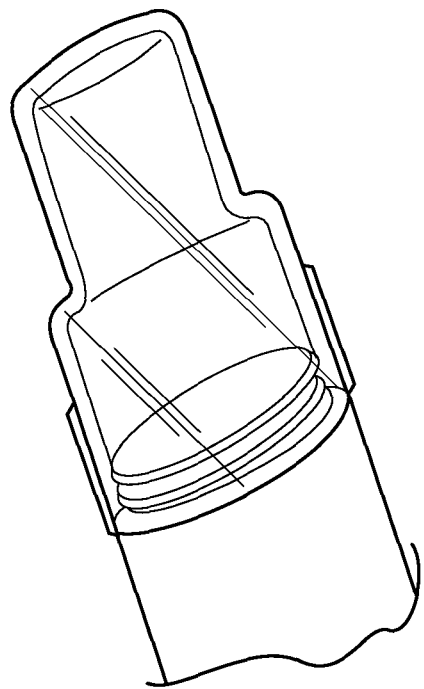
Figure 5E:
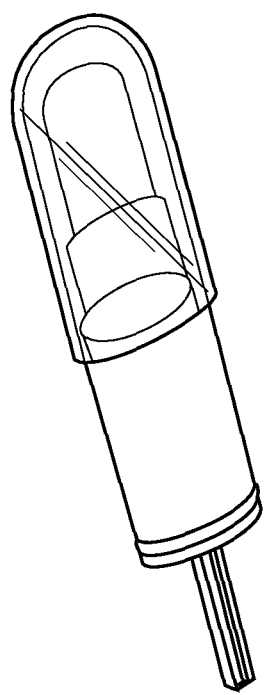
Figure 5F:
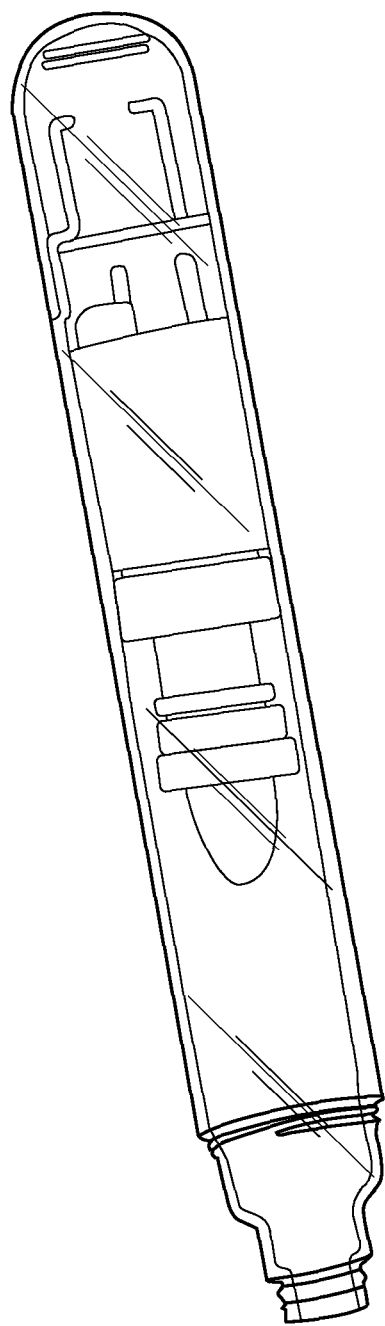

FIG. 4 is a schematic view of a second applicator embodiment showing an exploded view of all components. This embodiment includes an optional signal feature for verifying compliance with predetermined methods of using the applicator, such as, for example, a light, sound, and/or vibration to indicate that the microdevice has been applied to the skin with the recommended amount of force for perforating the outer layer of skin.

| Component | Name & Function |
|---|---|
| 001 | Outer Cap, gel agent end |
| 002 | Applicator Sleeve cap |
| 003 | Applicator Sleeve, active agent chamber |
| 004 | Outer Body |
| 005 | Applicator tip nozzle |
| 006 | Connector |
| 007 | Fixed Gear |
| 008 | Dial Ring |
| 009 | Dial tube that holds spring |
| 010 | Integrated Signal Device with timer, force switch and counter |
| 011 | Actuator Arm |
| 012 | FMA microdevice |
| 013 | FMA protective sleeve |
| 014 | Outer Cap, FMA microdevice end |
| 015 | Active agent reservoir |

The Actuator Arm 011 holds the FMA microdevice 012.

Gel/cream/lotion is dispensed from the applicator tip nozzle 002.

The Applicator Sleeve cap 002 and Applicator sleeve, active agent chamber 003 form a cavity to hold active agent(s). 002 and 003 are connected with a mechanical lock-in structure to facilitate the filling of active agent(s).

The Applicator tip nozzle 005 and Connector 006 are connected using a mechanical structure on the Connector 006. When the Dial tube 009 rotates, it passes the rotation to the Connector 006. The spiral structure on the Connector 006 pushes the Applicator tip nozzle 005 to move in the direction to push active agent(s) out through the gel nozzles. It moves the Applicator tip nozzle 005, acting like a piston, in the cavity formed by the Applicator sleeve cap 002 and the Applicator sleeve 003. The Dial Ring 008 and the Dial tube 009 are connected with a spring. Each dial of the Dial Ring 008 makes a sound between the Fixed Gear 007 and the Dial Ring 008.

The FMA protective sleeve 013 and the Dial tube 009 are connected. When the Outer cap, FMA microdevice end 014 rotates, the rotation is passed on through the FMA protective sleeve 013 to the Dial tube 009.

The two mechanical structures indicated by a red circle prevent the Fixed Gear 007 from moving forward so the Connector 006 moves forward when rotating FIG. 5 shows schematic views of the second applicator embodiment having a microdevice for painlessly perforating the outer layer of skin and a reservoir of active agent.

Example 3

FIG. 6 shows scanning electron microscope micrographs of examples of two different microneedle arrays having different microneedle sizes and density of microneedles. These microneedle arrays are examples of those that may be found on an applicator described herein.

Figure 7:
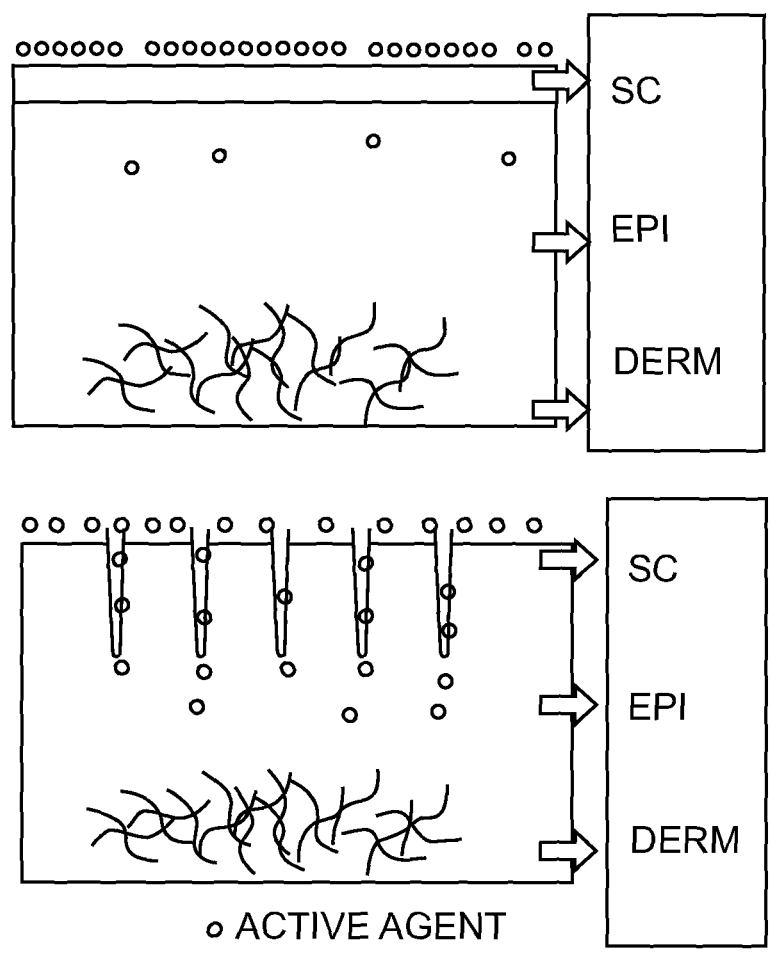
FIG. 7 is a perspective illustration showing the depth that the microdevice on the applicator perforates into the skin relative to the stratum corneum (SC), epidermis (Epi), and dermis (Derm), and the subsequent delivery of active agent applied to the area of skin that was perforated via microchannels generated by the microdevice.

FIG. 7 is a perspective illustration showing the depth that the microdevice on the applicator perforates into the skin relative to the stratum corneum (SC), epidermis (Epi), and dermis (Derm), and the subsequent delivery of active agent applied to the area of skin that was perforated via microchannels generated by the microdevice.

Example 4

Use of Applicators

The use of an applicator of the present subject matter was a simple two-step procedure. The first step was the perforation of skin using the microdevice attached to one end of the applicator, wherein the applicator is held in the hand and physical force is applied so that the microdevice end of the applicator causes the microdevice to perforate the skin. The amount of force applied to perforate the skin is also sufficient to move the actuator arm to contact and activate the switch on the integrated signal device. Activating the signal device resulted in a light to be illuminated. The user detected the light and recognized the light as indicating that the skin has been perforated. The user then immediately removed the applicator and microdevice from the skin. The second step was to apply the active agent to the area of skin perforated by the microdevice. After removing the microdevice, the user then turned the applicator around and applied an active agent formulation from a nozzle attached to that end of the applicator. The active agent is contained in an active agent chamber contained in the body of the applicator. Thus, the active agent was applied to the area of skin perforated by the microdevice. Optionally, the microdevice end was swabbed or immersed in a disinfectant solution or cream. End caps were then placed over both the microdevice region and the applicator nozzle region for storing the applicator.

Example 5

Use of Applicators in Pain Management

A applicator described herein may be used in pain management. Lidocaine, an anesthetic agent, is used as the active agent and can penetrate skin 10 times faster on a applicator pre-treated skin. Pain management using the applicator provided herein, as compared to prior art, has at least these two advantages: (1) rapid onset, and (2) about ten times improvement in percutaneous drug delivery.

Example 6

Use of Applicators in Cosmetic Treatment

A applicator described herein may be used in cosmetic treatment. L-Carnitine, is used as the active agent and can penetrate skin 10 times faster on applicator pre-treated skin. Cosmetic cellulite management using the applicator provided herein, as compared to prior art, has at least these two advantages: (1) rapid onset, and (2) about ten times improvement in percutaneous drug delivery.

L-carnitine (LC) is a naturally occurring compound used by the body to transport long-chain fatty acids across inner mitochondria membrane for β-oxidation. It is a nutrient essential for energy production and fat metabolism in skeletal muscle and heart [1]. More than 95% of human body's total carnitine is in myocardium and skeletal muscle [2]. In recent years, LC has been extensively used as a medicine in the treatment of carnitine deficiency disorders [3, 4], a variety of cardiovascular symptoms [1, 5] and the prevention of drug-induced myopathies in patients with HIV infection [6]. Furthermore, many researchers found that supplementation of LC have potentially beneficial effects on athlete performance [7], obesity [8], liver healthy [9], hemodialysis [10], male infertility [11] and diabetes [12].

In this example, a detailed investigation is provided of percutaneous transport of LC by using an applicator with a painless Functional MicroArray (FMA) with microneedles of 150 μm length. In vitro study evaluated the effects of different species of skins, donor concentration and gel formulations on the permeability of LC by FMA intradermal delivery system. In vivo study assessed the absolute bioavailability and pharmacokinetic profile of topical gel patch of LC, comparing with intravenous and oral administration, to indicate the efficacy of FMA for LC percutaneous administration. The enhancement of LC bioavailability by FMA is the major discovery of this work.

Materials and Methods
Chemicals and Reagents

LC ((3R)-3-hydroxy-4-trimethylazaniumylbutanoate, MW 161.2 Da), Carbomer 940 P (CP940), Carbomer 974 P (CP974), Carbomer 980 P (CP980) and Carbomer 1342 P (CP1342) were all purchased from GuoRenYiKang Technology (Beijing, China). HPLC grade methanol was obtained from Dikma Technology (Beijing, China). All solutions were prepared with ultrapure water (resistivity>18 MΩ/cm). All chemicals used were analytical or pharmaceutical grade.

Functional MicroArray System (FMA)

The Functional MicroArray system has been described previously without modification (22, 23). Each FMA has 484 microneedles perpendicular to the wafer, over an area of 10×10 $mm^2$. Each microneedle has an octagonal pyramidal shape. They are 150 μm in height, with a base length of about 100 μm, a cone angle of 38° and a needle tip less than 100 nm. The FMA was fixed onto the supporting mechanism of an applicator to form an intradermal drug delivery system, which provided an insertion force of approximately 2 N.

Preparation of Carbomer Hydrogels

Hydrogels of LC were prepared using Carbomer polymers, including. CP940, CP974, CP980 and CP1342. Briefly, at a concentration of 0.5% (w/w) of Carbomers were added to ultrapure water with vigorous mixing and the dispersion was allowed to hydrate and swell for about 2 h. Then the gels were formed by dropwise addition of triethanolamine (0.8% w/w) to neutralization. Finally, appropriate amount of LC powder was dissolved in the above gels with stirring at room temperature.

Skin Preparation In Vitro

Male Sprague-Dawley rats (220-250 g) were provided by Beijing Weitong Lihua Experimental Animals Ltd. Co. (Beijing China). Forty-eight hours before the test, rats were anesthetized by ether, and then the abdominal hair of each rat was shaved with an electric hair clipper. At the beginning of in vitro studies, animals were euthanized using carbon dioxide and full-thickness skins were removed. All research protocols adhered to the Guide for the Care and Use of Laboratory Animals (1996).

Samples of full-thickness dermatomed human cadaver skins (≈800 μm) were obtained from the Burns Institute, $304^{th}$ Clinical Department, The General Hospital of PLA, Trauma Center of Postgraduate Medical College and were free from overt pathology. The skin samples were kept frozen in liquid nitrogen and used within 3 months.

Porcine ear skins (adult pig) were purchased from a local slaughterhouse immediately following the animal death and the whole skins were carefully dermatomed to a thickness of 800 μm with skin grafting knife. The excised porcine ear was wrapped in plastic film and stored in liquid nitrogen until use within 3 months.

In Vitro Permeation Study

The method of the percutaneous absorption study adheres to the Test Guideline 428 of Organization for Economic Cooperation and Development (2004). The experiment was performed with a system employing Franz-type glass diffusion cells. The temperature in the receptor chamber was maintained at physiological temperature of 37.0±0.1° C. with an external, constant temperature circulating water bath.

Skin samples were treated using FMA delivery system. The insertion force was provided by the applicator. The skins without FMA treatment were used as control. The skin was mounted on a receptor chamber (2.5 ml) with the stratum corneum side facing upward into the donor chamber with effective permeation area of 0.66 $cm^2$. The receptor and donor chambers were filled with PBS solution, and the receptor fluid was continuously stirred with a magnetic bar at 280 rpm to maintain homogeneity. After 1 h equilibration, the solution in the receptor chamber was replaced with fresh PBS, and 300 μl of LC solution or 300 mg of LC gel was applied on the skin in the donor chamber, which was then covered with a parafilm to avoid any evaporation process. The samples of receptor cell were withdrawn through at predetermined time intervals and the receptor phase was immediately refreshed by equal volume of PBS buffer to keep a constant volume. The samples were analyzed by HPLC/UV. The results were expressed as the mean±S.D. (n=3-4 independent samples).

In Vivo Permeation Study

Male Sprague-Dawley rats (250 g±10 g) were equally divided into four groups (3 for each): group A, B, C and D. Before administration, all rats allowed to acclimatize for one week. One day before administration, rats were fasted overnight but allowed access to water. The hair of abdominal skin was carefully shaved by electric clippers for Group A and B. The rats in group A were pretreated by FMA with an area of 2 $cm^2$, the group B was untreated as a control. Then hydrogel patch containing LC 750 mg was applied to each rat by an adhesive housing for 6 h. Group C and Group D were control groups of oral and intravenous injection administration of 1 ml LC solution (200 mg/ml). A volume of 0.5 ml blood samples were taken before administration and at predetermined time intervals after LC administration. Plasma samples were immediately separated by centrifugation at 4000×g for 7 mins, and stored at −80° C. until assay.

Patch Residual Assay of LC

To determine the apparent dose of LC delivered from gel patch in vivo study, patches were collected after 6 h application, and stored at 4° C. until assay. Each patch was transferred into a suitable flask and ultrapure water was added. The mixture was shaken for 20 mins, and then centrifuged for 8 min at 10000×g. Supernatant solution was analyzed by HPLC/UV. Apparent dose of LC delivered was calculated as difference between initial and residual drug content in patch.

Assay Methods

In Vitro

The quantitative determination of LC was performed by HPLC using methanol-190 mM $KH_2PO_4$ water (87:13) as mobile phase at a flow rate of 0.6 ml/min, by LC-2010A (Shimadzu, Japan). The injection volume was 20 μl. The analysis was performed in a YMC-Pack ODS-A C18 column with dimensions of 250 mm×4.6 mm i.d., 5 μm particle size (YMC Inc., USA). The column eluant was monitored at 225 nm. The detection limit is 20 μg $ml^{-1}$. The inter- and intra-day variability was less than 5%.

In Vivo

Pretreatment method of samples: 120 μl of plasma was deproteinized with 600 μl of 0.6 M perchloric acid. The mixture was shaken for 30 s and allowed to stand in an ice bath for about 15 mins. After centrifuged at 4000×g for 7 mins, 500 μl of supernatant was transferred to a new tube in which 300 μl of 0.5 M $K_2CO_3$ was added, the mixture was shaken for 30 s and incubated in an ice-bath for 15 mins. Precipitate of $KClO_4$ was removed by centrifugation at 4000×g for 7 mins, and 200 μl of the supernatant with free LC was separated for the assay. The recovery ratio of LC in plasma was 85±2%.

Assays: The concentration of free LC in serum was determined by enzymatic assay kit with a limitation detection of 0.8 μg/ml. (BIOSENTEC France), Cat. No. 066.

Calculations and Statistical Analysis

In Vitro

The cumulative amount of drug permeated per unit area versus time was plotted. The permeation rates of LC were calculated from the slope of linear portion of the plots. Data analysis was carried out with Microsoft Excel, Version 2000. Results were presented as the mean±S.D. (n=3-4 independent samples). Statistically significant differences were determined using the analysis of variance (ANOVA) with P<0.05 as a minimal level of significance.

In Vivo

Maximum plasma concentration ($C_{max}$) and the time to reach this peak ($T_{max}$) were directly identified from the pharmacokinetic curves (LC plasma concentration versus time). Area under the plasma concentration-time curve ($AUC_{0\rightarrow\infty}$) was calculated by using the trapezoidal rule. Absolute bioavailability (A.B.) of LC after oral and FMA administration comparing with intravenous administration was calculated using the following equation:

$$\text{Absolute bioavailability}\,(A.B.) = \frac{AUC_{FMA/oral}}{dose_{FMA/oral}} \times \frac{dose_{iv.}}{AUC_{iv.}} \times 100$$

Results and Discussion

In Vitro Percutaneous Delivery of LC through the skins of Different Species

Figure 8:
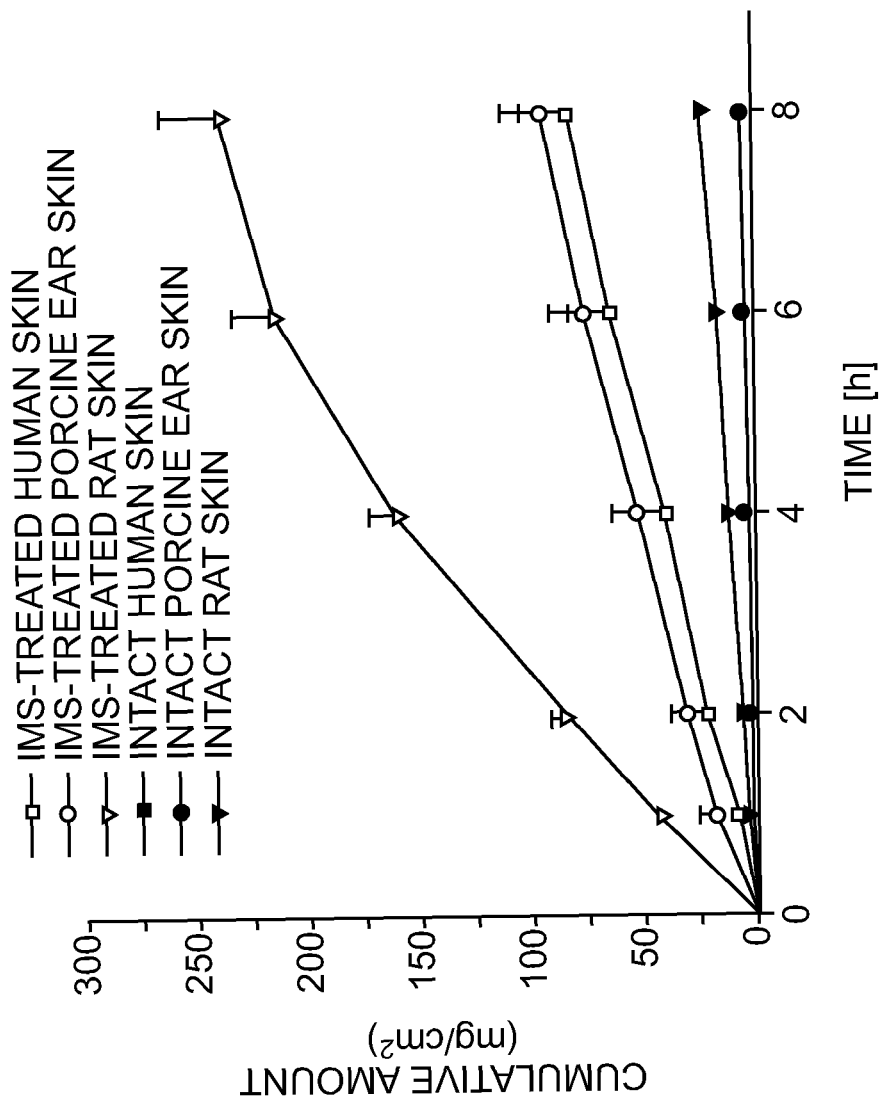
FIG. 8. The LC profiles of cumulative amount vs. time using skins of different species with and without FMA-assisted delivery. Mean±S.D., n≥3. Each donor concentration was 640 mg/mL.

Firstly, the effect of skins from different species on LC permeability was investigated. As indicated in FIG. 8, the highest cumulative amount of LC over 8 h by passive diffusion could be seen for rat skin. After pretreatment with FMA, the cumulative amount of LC was greatly enhanced for all skins, and it was similar between human and porcine ear skin.

The results of percutaneous delivery of drug are influenced by skin of different species. Human skin is considered as the best material for in vitro experiment, but its availability and proper storage is sufficient challenge. Fortunately, a wide range of animal skin models have been well established as alternatives to human skin. These animal skin models include rat, mouse, rabbit, pig, guinea pig and snake skins. However, there may be variation in the drug permeability of various skins. So, it is necessary to evaluate the effect of skin model used in the study of a new drug delivery method and its proper formulation.

Table 1 shows the permeation rates of LC across different species of skins by passive diffusion or with FMA pretreatment. The permeation rates of LC by FMA were significantly enhanced in all species of skins comparing with passive diffusion. The permeation rate of LC through human skin was enhanced 59 times comparing with passive diffusion and was nearly the same with porcine ear skin, but there were significant differences between human and porcine ear skin by passive diffusion (p<0.05). Furthermore, the permeation rates of LC through rat skin was about 13.8 times higher than that of human skin by passive diffusion, and the enhancement was only 3.7 times after FMA-puncture. According to the above results, it was implied that FMA may reduce the interspecies variations in skin permeability. Some researches have indicated that iontophoretic enhancement technique could reduce the interspecies differences in percutaneous permeation of drugs [25, 26]. The results of present study were similar to above observations. The explanation may be that FMA-puncture provides new aqueous micron-pores [27], which turned to be the main pathway to transport molecules, especially to the extremely hydrophilic drug LC. Therefore, differences among the resistance of various species of skin were decreased.

TABLE 1

Permeation rates and enhancement ratio (ER) of LC across different species of skins with and without FMA delivery system.

| Skin type | Thickness | Permeation rates (mg/cm²/h) | | ER (%) |
|---|---|---|---|---|
| | | FMA | Passive Diffusion | |
| Human | Dermatomed ≈ 800 μm | 10.65 ± 2.12 | 0.18 ± 0.02 | 59 |
| Porcine ear | Dermatomed ≈ 800 μm | 11.08 ± 2.05 | 0.37 ± 0.04 | 30 |
| Rat | Full thickness | 40.16 ± 3.97 | 2.49 ± 0.40 | 16 |

Enhancement ratio (ER),
FMA permeation rates/passive permeation rates
Data are mean ± S.D., n ≥ 3

In Vitro Effect of Donor Concentration

Figure 9:
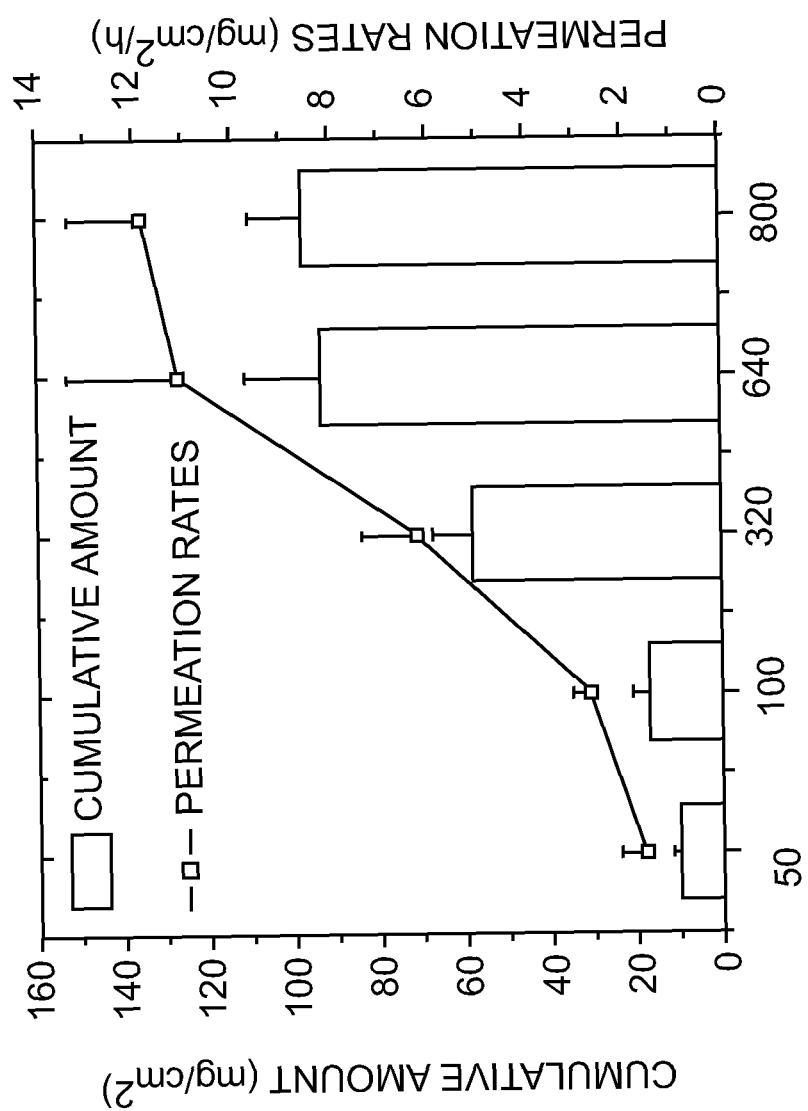
FIG. 9. The effect of different LC donor concentration on the LC cumulative amount and permeation rates through porcine ear skin by FMA delivery system during 8, mean±S.D., n=3.

Further experiments were carried out using porcine ear skin pretreated by FMA because the peameability of LC through porcine ear skin is close to human skin. The influence of drug concentration on the FMA intradermal transport of LC was presented in FIG. 9. The permeability of LC increased with increasing donor concentration until 640 mg/ml. In summary, the cumulative amount and permeation rates of LC were not significantly different between 650 mg/ml (93.23±17.76 $mg/cm^2$ and 11.08±2.05 $mg/cm^2/h$) and 800 mg/ml (97.20±12.60 $mg/cm^2$ and 11.80±1.50 $mg/cm^2/h$) (P>0.05). The results show that there may be a certain threshold of FMA transport, since increasing donor concentration was no longer resulted in increase of drug transport. This type of cut-off phenomenon has been reported in microneedle-mediated percutaneous delivery of human IgG [28]. This may be due to the transport pathway of the drug through the skin is saturated at a higher concentration.

In Vitro Effect of Different Type of Carbomer Polymers

At present, numerous grades of Carbomer polymer are commonly available for the percutaneous hydrogel formulations because of their low irritation and high viscosity at low concentration. Different types of Carbomer varying in cross-link density and molecular weight could influence the diffusion pathway and drug release [29]. The influence of different carbomer polymers (eg: CP940, CP974, CP980, CP1342) on the permeability of LC was studied across porcine ear skin. Skin was pretreated by FMA and LC hydrogel (640 mg/g) was applied to each donor.

Figure 10:
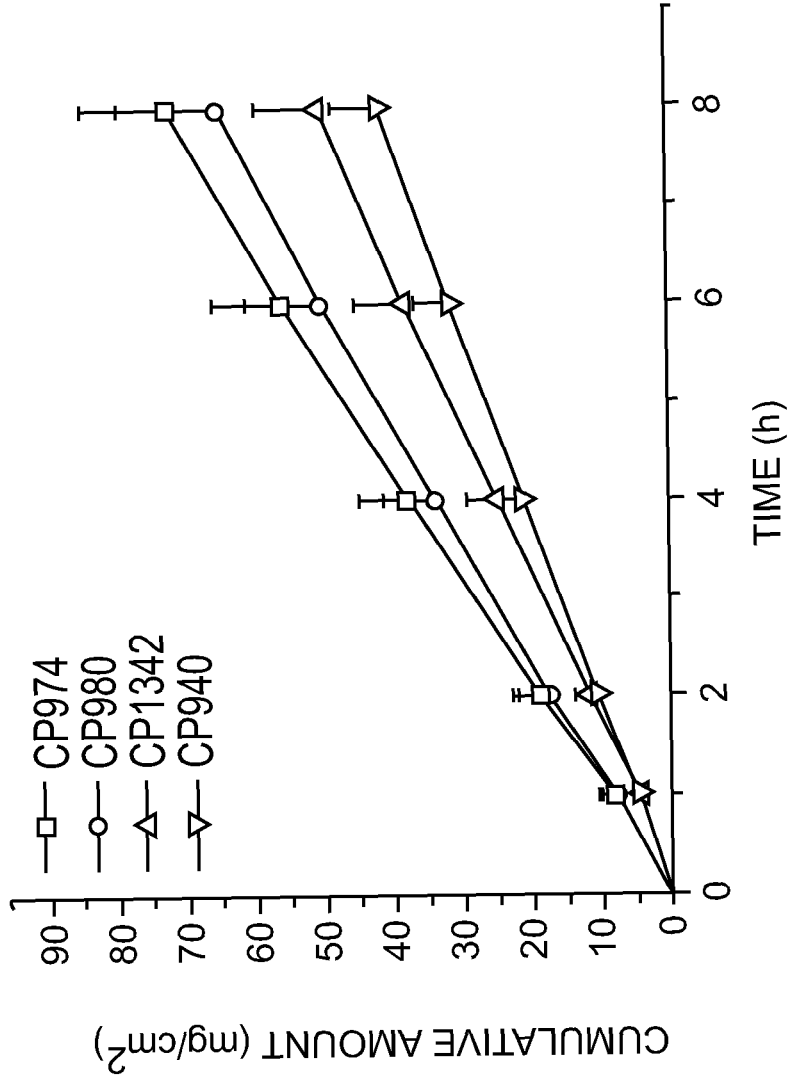
FIG. 10. Diffusion profiles of the gels with different type of carbomer polymers on the release of LC across porcine ear skin by FMA-treated, mean±S.D., n=4.

FIG. 10 illustrates the cumulative amount of LC penetrated from the various kinds of Carbomer formulations. Total cumulative amount of LC from CP980 and CP974 were significantly higher than that from CP1342 and CP940 (P<0.05). Furthermore, there was no significant difference between the cumulative amount from CP974 (71.78±12.44 mg/cm$^2$) and CP980 (64.43±14.48 mg/cm$^2$) (P>0.05). It was noteworthy that the viscosity of CP980 calculated by rheological synergism was significantly higher than CP974 [30]. Therefore, gel containing CP 980 was elected as a suitable carrier for topical application of LC.

In Vivo Assessment of Apparent Dose of LC Delivered into Rats from Gel Patch

The residual content of drug in the patch was investigated to assess the apparent LC dose delivered by applying topical gel formulation CP980 (750 mg/rat) to rats with and without FMA pretreatment.

Table 2 presents the mean apparent dose of LC gel patch delivered after 6 h topical application with and without FMA pretreatment. About 27% of initial amount of LC was delivered into rats by FMA pretreatment, totaling 200 mg/rat. However, there was no significant difference between the residual and initial content by passive diffusion. These results showed that FMA intradermal delivery successfully allowed much higher apparent dose of LC delivery than traditional percutaneous delivery. It implied that FMA intradermal delivery system could solve the problem of high dose requirement for LC.

TABLE 2

Summary of apparent dose of LC delivered with and without FMA delivery system.

| Parameters | With FMA | Without FMA |
| --- | --- | --- |
| Total amount of LC in patch (mg/rat) | 750 | 750 |
| The residual amount (mg/rat) | 550 | 764 |
| Apparent dose of LC (mg/rat) | 200 | ND |
| LC delivered (%) | 27% | ND |

ND: not determined

Phamacokinetics and Absolute Bioavailability of LC

Figure 11:
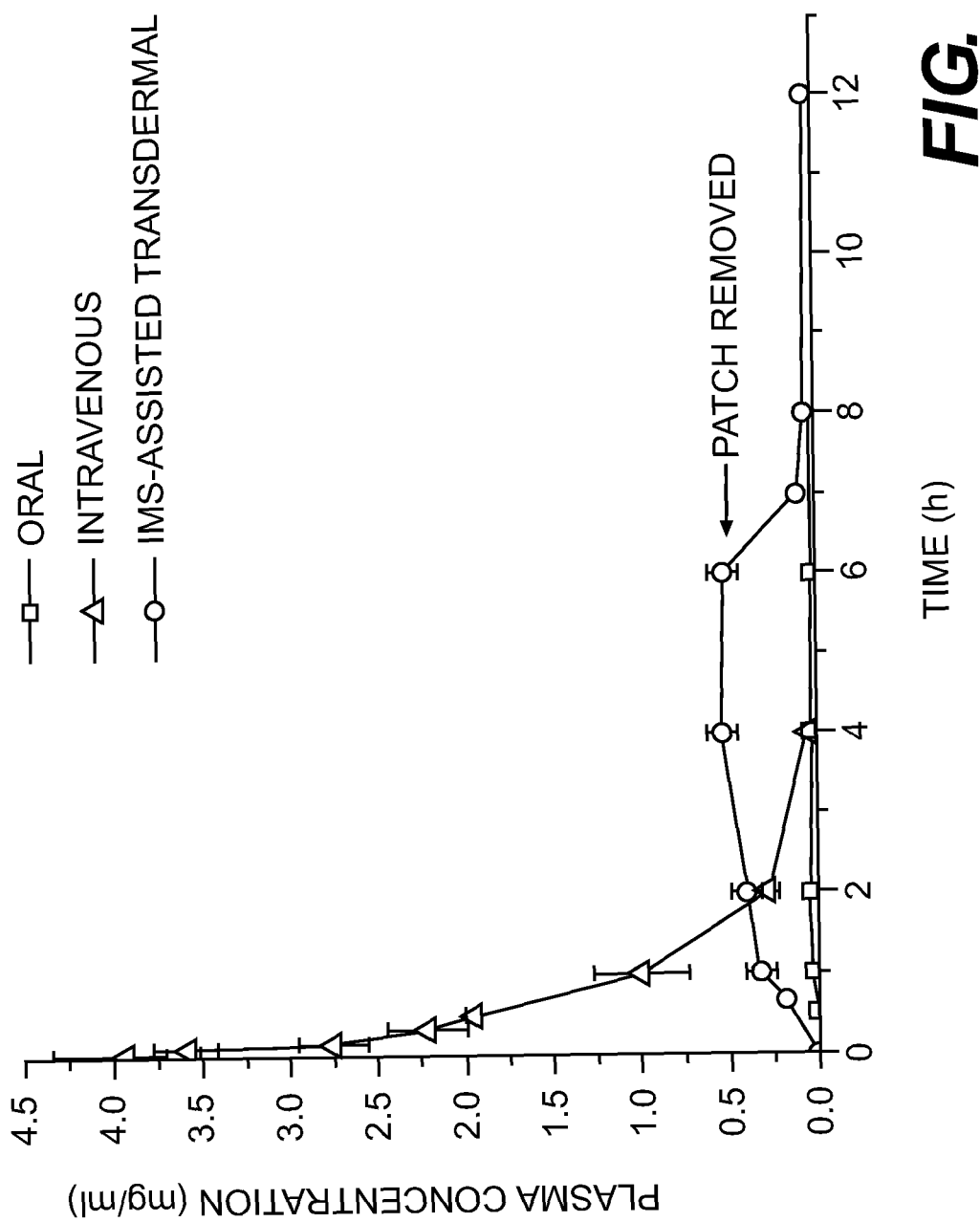
FIG. 11. Mean plasma concentration versus time profiles of LC after single intravenous (200 mg/rat), oral (200 mg/rat), and FMA percutaneous administration (750 mg/rat; 2cm2), mean±S.D., n=3.
Figure 12:
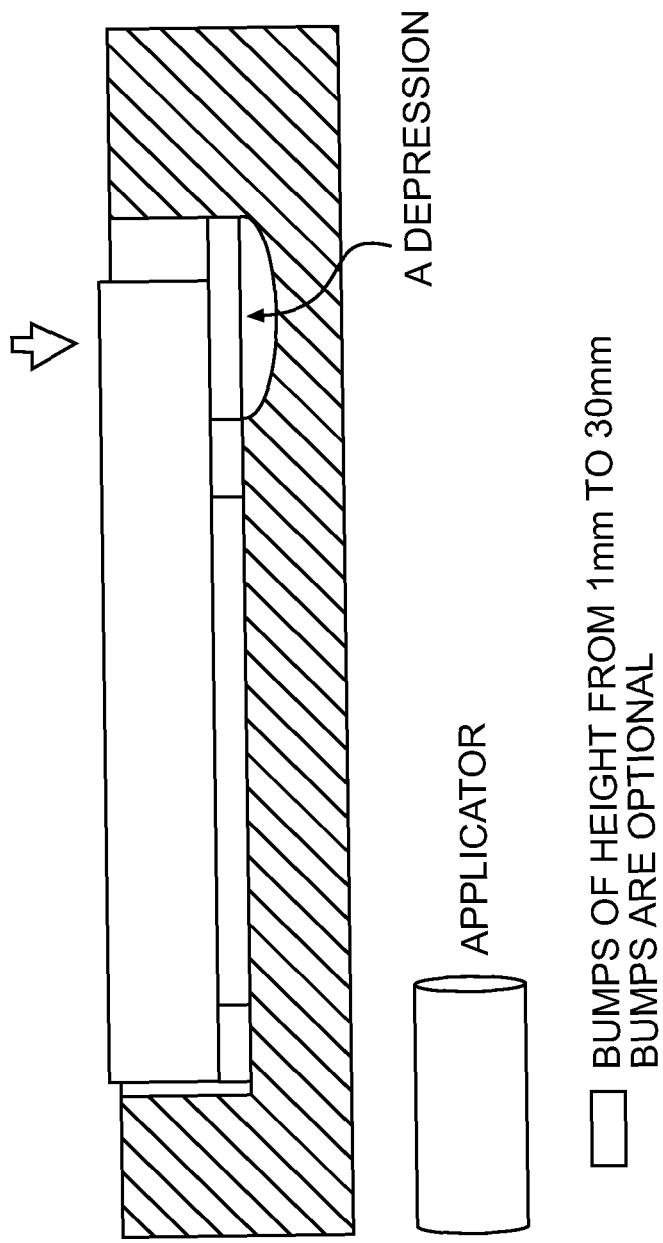
FIG. 12 shows a cross-sectional view of the applicator in a package with one side of the applicator over a depression.
Figure 13:
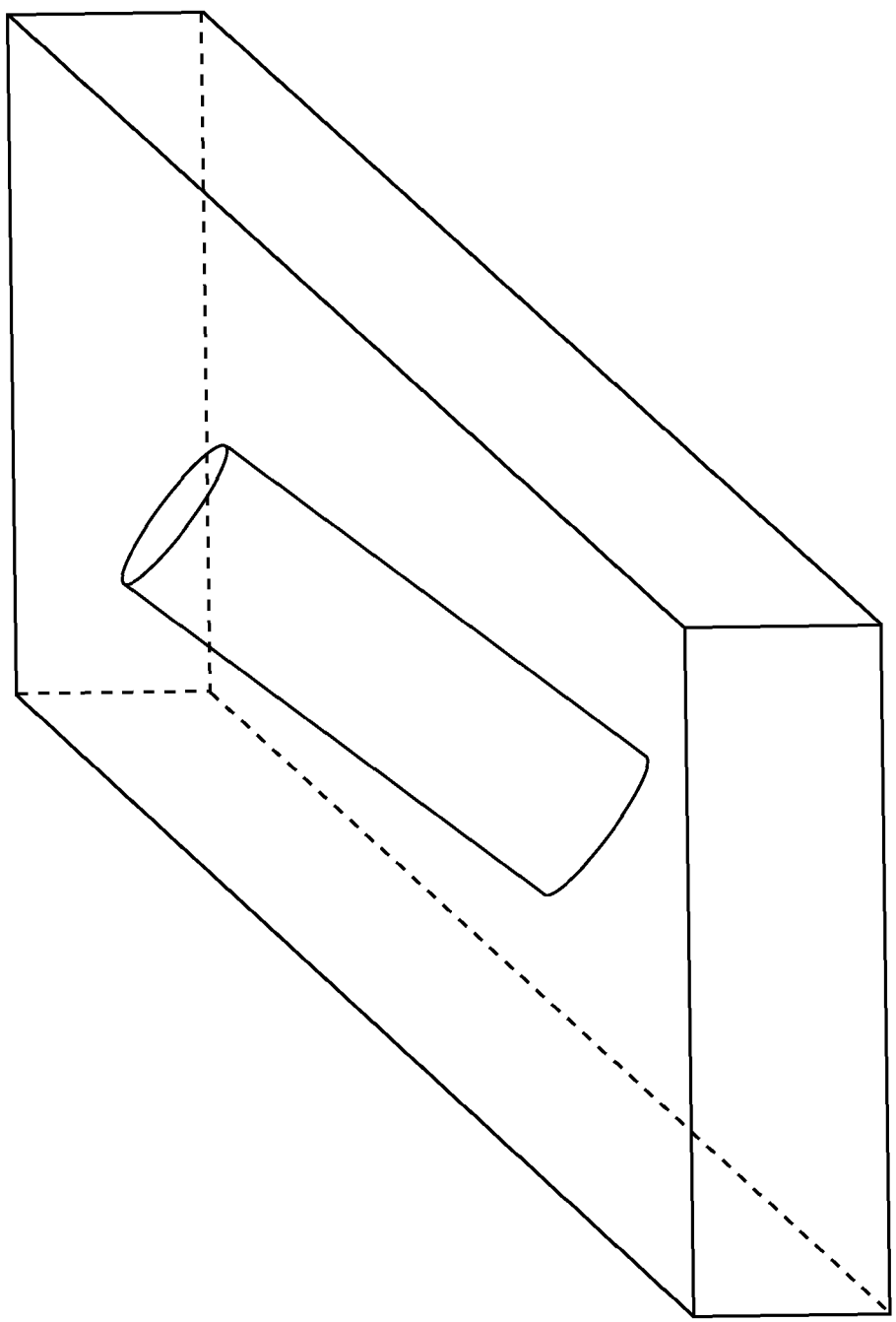
FIG. 13 provides a 3D illustration of the applicator in its packaged box.

FIG. 11 shows the plasma concentration-time profiles of LC after intravenous (200 mg/rat), oral (200 mg/rat) and FMA percutaneous administration (750 mg/rat). The corresponding pharmacokinetic parameters are summarized in Table 3.

TABLE 3

Pharmacokinetic parameters of LC determined after single oral and FMA-assisted percutaneous administration.

| | Dosage | $C_{max}$ (mg/ml) | $T_{max}$ (h) | $AUC_{0-\infty}$ (mg·h·L$^{-1}$) | A.B. (%) |
| --- | --- | --- | --- | --- | --- |
| Intravenous | 200 mg/rat | — | — | 3677 | 100 |
| Oral | 200 mg/rat | 0.040 (0.013) | 2 | 309 | 8.0 |
| FMA delivery | 750 mg/rat | 0.53 (0.086) | 4 | 3049 | 22.0 |

Table 3 can cause confusion as FMA dose is more than 3 times than that of oral and intravenous. We can say AUC is more than 10 times than that of oral.

After intravenous administration, the plasma concentration was up to 3.90±0.42 mg/mL at 3 min, but rapidly decreased to 0.27±0.05 mg/mL at 2 h. Oral administration brought low plasma levels, and the plasma concentration peaked at 2 h (0.040±0.011 mg/mL). The absolute bioavailability was 8%. Comparing with oral administration, higher plasma concentrations were obtained by using FMA intradermal delivery system. At the same time, the $AUC_{0-\infty}$ was 3016 mg.h.L$^{-1, 10}$-fold higher than that of oral administration and the absolute bioavailability was 22%. A maximum concentration ($C_{max}$) of 0.53±0.086 mg/mL was achieved at 4 h, which was about 13-fold higher than that following oral administration. Furthermore, the plasma level was maintained relatively smooth from 1 h to 6 h in the range of 0.33 mg/mL to 0.51 mg/mL. After patch removal, plasma level of LC rapidly declined, suggesting LC percutaneous delivery into the corium and into systemic circulation. Pharmacokinetic study demonstrated that, after FMA intradermal administration, the absorption of LC was stable over the whole administration period of 6 h comparing with intravenous application. It is notable that absolute bioavailability for LC FMA intradermal delivery was approximately 2.8 times higher than oral application. A variety of experiments, including human [31] and rats [14, 15], have concluded that the low bioavailability of oral delivered LC has been ascribed to poor absorption across the intestinal epithelium. Hence, it is easy to understand that the bioavailability of LC following FMA intradermal delivery would be higher than oral administration because of its direct absorption via blood vessels among dermal layer. Therefore, FMA intradermal delivery administration would provide a new and effective administration strategy for enhancing bioavailability of LC, and potentially improve patient compliance with additional benefits such as controlled stable release of drugs to minimize toxicity while maximizing therapeutic outcome.

Conclusions

The present work illustrated that FMA painless intraepidermal delivery system could be used for percutaneous administration of LC. In vitro studies indicated that the LC permeability with FMA-assisted transport across different skins was significantly increased comparing with passive diffusion, and permeation across human skin was about 59 times higher than passive diffusion. The pharmacokinetic study showed that FMA intradermal delivery of LC gel patch would give a relative smooth and continuous plasma levels comparing with conventional dosage forms. A 2.8-fold enhancement of absolute bioavailability was obtained comparing with oral administration. In summary, FMA intradermal delivery system represents a promising and beneficial method for LC administration and can be possibly extended to other high hydrophilic drugs. Further studies should be conducted to probe the tissue concentration of LC in rat tissues (e.g.: muscle, heart, kidney and liver) by FMA intradermal delivery.

References

[1] S. Sharma, S. M. Black. Carnitine homeostasis, mitochondrial function and cardiovascular disease. Drug Discovery Today: Disease Mechanisms in Press, corrected Proof (2009).

[2] A.Gvozdjáková. Carnitine. In A.Gvozdjáková. (eds.), Mitochondrial Medicine, Springer Netherlands, Netherlands, 2008, pp. 357-366.

[3] R. Pons, D. C. De Vivo. Primary and secondary carnitine deficiency syndromes. J. Child. Neurol. 10:S8-24 (1995).

[4] Jusié A. Carnitine: physiologic role, primary and secondary deficiency, *Lijec Vjesn.* 114:166-171 (1992).

[5] A. A. Michael. Carnitine and its derivatives in cardiovascular disease. Prog. Cardiovasc. Dis. 40:265-286 (1997).

[6] I. Ilias, I. Manoli, M. R. Blackman, P. W. Gold, S. Alesci. L-Carnitine and acetyl-L-carnitine in the treatment of complications associated with HIV infection and antiretroviral therapy. Mitochondrion. 4:163-168 (2004).

[7] E. P. Brass, C. L. Hoppel, W. R. Hiatt. Effect of intravenous L-carnitine on carnitine homeostasis and fuel metabolism during exercise in humans. Clin. Pharmacol. Ther. 55:681-692 (1994).

[8] K. D. Wutzke, H. Lorenz. The effect of l-carnitine on fat oxidation, protein turnover, and body composition in slightly overweight subjects. Metabolism. 53: 1002-1006 (2004).

[9] B. Chang, M. Nishikawa, S. Nishiguchi, M. Inoue. L-carnitine inhibits hepatocarcinogenesis via protection of mitochondria. Int. J. Cancer. 113:719-729 (2005).

[10] S. Ahmad. L-Carnitine in Dialysis Patients. Seminars in Dialysis. 14: 209-217(2001)

[11] M. Costa, D. Canale, M. Filicori, S. D'Lddio, A. Lenzi. L-carnitine in idiopathic asthenozoospermia: a multicenter study. Andrologia. 26:155-159 (1994).

[12] G. Mingrone, A. V. Greco, E. Capristo, G. Benedetti, A. Giancaterini, A. De Gaetano, G. Gasbarrini. L-carnitine improves glucose disposal in type 2 diabetic patients. J. Am. Coll. Nutr. 18:77-82 (1999).

[13] A. M. Evans, G. Fornasini. Pharmacokinetics of L-carnitine, Clin. Pharmacokinet 42:(2003) 941-967.

[14] H. Gudjonsson, B. U. Li, A. L. Shug, W. A. Olsen. Studies of carnitine metabolism in relation to intestinal absorption. Am. J. Physiol. 248:G313-319 (1985).

[15] C.J. Rebouche, D. L. Mack, P. F. Edmonson. L-Carnitine dissimilation in the gastrointestinal tract of the rat. Biochemistry. 23:6422-6426 (1984)

[16] P. Harper, C. E. Elwin, G. Cederblad. Pharmacokinetics of bolus intravenous and oral doses of L-carnitine in healthy subjects. Eur. J. Clin. Pharmacol. 35:69-75 (1988).

[17] E.P. Brass. Pharmacokinetic considerations for the therapeutic use of carnitine in hemodialysis patients. Clin. Ther. 17:176-185 (1995).

[18] J. Schulz, R. Kroepke, A. Schepky, J. Eckert, U. Koop, S. Faenger. Cosmetic combination product for improving appearance. U.S. patent Ser. No. 11/839,384, Aug. 28, 2008

[19] Madison Metabolomics Consortium Database, http://mmcd.nmrfam.wisc.edu/test/cqsearch.py?cqid=cq_09878)(assessed 10/01/09).

[20] M. I. Haq, E. Smith, D. N. John, M. Kalavala, C. Edwards, A. Anstey, A. Morrissey and J. C. Birchall. Clinical administration of microneedles: skin puncture, pain and sensation. Biomed. Microdevices. 11:35-47 (2009).

[21] Y. Xie, B. Xu, Y. Gao. Controlled transdermal delivery of model drug compounds by MEMS microneedle array. Nanomed. 1:184-190 (2005).

[22] Y. Qiu, Y. Gao, K. Hu, F. Li. Enhancement of skin permeation of docetaxel: a novel approach combining microneedle and elastic liposomes. J. Control. Release. 129:144-150 (2008).

[23] Y. Wu, Y. Qiu, S. Zhang, G. Qin, Y. Gao. Microneedle-based drug delivery: studies on delivery parameters and biocompatibility. Biomed. Microdevices. 10:601-610 (2008).

[24] X. Li, R. Zhao, Z. Qin, J. Zhang, S. Zhai, Y. Qiu, Y. Gao, B. Xu, S. Thomas. Microneedle pretreatment improves efficacy of cutaneous topical anesthesia. Am J Emerg Med. doi:10.1016/j.ajem.2008.10.001.

[25] N. Kanikkannan, J. Singh, P. Ramarao. transdermal iontophoretic transport of timolol maleate: effect of age and species. J. Control. Release. 71:99-105 (2001).

[26] R. van der Geest, M. Danhof, H. E. Bodde. Iontophoretic delivery of apomorphine. I: In vitro optimization and validation. Pharm. Res. 14:1798-1803 (1997).

[27] A. L. Stinchcomb, S. L. Banks. Methods and compositions for enhancing the viability of microneedle pores. U.S. patent Ser. No. 12/325,919, Jun. 4, 2009.

[28] G. Li, A. Badkar, S. Nema, C. S. Kolli, A. K. Banga. In vitro transdermal delivery of therapeutic antibodies using maltose microneedles. Int. J. Pharm. 368:109-115(2009).

[29] T. Macedo, L. H. Block, A. J. Shukla. Release of tolmetin from carbomer gel systems. Drug Dev. Ind. Pharm. 19:887-902 (1993).

[30] J. Ceulemans, A. Ludwig. Optimisation of carbomer viscous eye drops: an in vitro experimental design approach using rheological techniques. Eur. J. Pharm. Biopharm. 54:41-50 (2002).

[31] K. Matsuda, H. Yuasa, J. Watnabe. Physiological mechanism-based analysis of dose-dependent gastrointestinal absorption of L-carnitine in rats. Biopharm. Drug Dispos. 19:465-472 (1998).

While particular embodiments of the present subject matter have been shown and described, it will be obvious to those skilled in the art that changes and modifications can be made without departing from this subject matter in its broader aspects. Therefore, the appended claims are to encompass within their scope all such changes and modifications as fall within the true spirit and scope of this invention.

What is claimed:

1. An applicator with at least one built-in non-verbal instructional device comprising:
a hollow body structure having a first end and a second end, and having an exterior surface and an interior surface;
said first end of said body structure comprising a microdevice for perforating only the skin's stratum corneum layer for intraepidermal delivery of active agents and at least one built-in non-verbal instructional device to elicit correct behavior, rectify incorrect behavior and improve user compliance by producing instructional signals signifying one or more of the number of applications, the force of each application to validate each application, and the duration of each application;
said second end of said body structure comprising at least one opening to allow dispensing of an active agent, that can treat certain diseases, directly to an area of perforated skin from the second end and/or at least one opening to allow dispensing of pigments or inks, to temporarily change the appearance of skin, directly to the area of perforated skin from the second end.

2. The applicator according to claim 1, wherein the second end further comprises an active agent reservoir containing at least one active agent and an active agent applicator portion configured to release the active agent directly onto the area of perforated skin.

3. The applicator according to claim 2, wherein the microdevice comprises a plurality of high-aspect-ratio microneedles, microblades, microknives, or combinations thereof.

4. The applicator according to claim 3, wherein the microneedles, microblades, or microknives have a length ranging from 4 to 500 microns.

5. The applicator according to claim 3, wherein the microneedles, microblades, or microknives have a length ranging from 10 to 200 microns.

6. The applicator according to claim 3, wherein the microneedles, microblades, or microknives have a length ranging from 20 to 100 microns.

7. The applicator according to claim 3, wherein the microneedles, microblades, or microknives are distributed on the surface of the microdevice at a density ranging from 20 per $cm^2$ to 20,000 per $cm^2$.

8. The applicator according to claim 3, wherein the microdevice has an area ranging from 1 $mm^2$ to 2500 $mm^2$.

9. The applicator according to claim 2, further comprising at least one indicator signal device that can provide a signal selected from the group consisting of a light signal, a sound signal, a vibration signal, a recorded counter signal, an RF transmitted signal, an electric transmitted signal, and a combination thereof.

10. The applicator according to claim 9, wherein the signal device is activated and a signal generated when the microdevice is applied to the skin with the recommended amount of force for perforating the skin.

11. The applicator according to claim 2, wherein the at least one active agent is selected from the group consisting of a therapeutic agent, a cosmetic agent, a vaccine and a combination thereof.

12. The applicator according to claim 2, wherein the at least one active agent is formulated in a hydrogel form.

13. The applicator according to claim 12, wherein the at least one active agent formulated in hydrogel form comprises at least one carbomer polymer.

14. The applicator according to claim 2, wherein the at least one active agent is applied to the skin by way of an applicator nozzle connected directly or indirectly to the active agent reservoir.

15. The applicator according to claim 2, wherein at least one active agent is applied to the skin by way of an absorbent applicator swab attached directly or indirectly to the active agent reservoir.

16. The applicator according to claim 2, wherein the at least one active agent is mechanically dispensed in a measured amount from the active agent reservoir before being applied to the skin.

17. The applicator according to claim 2, wherein the release of the active agent is controlled or metered.

18. The applicator of claim 1, wherein the second end further comprises a connector that attaches to a personal communication device, personal entertainment device, writing device, knife, scissors, clump, pen sharpener, key chain, magnetic bar, cartoon head, decoration object or a toy.

19. An applicator with at least one built-in non-verbal instructional device comprising:
a hollow body structure having a first end and a second end, and having an exterior surface and an interior surface;
said first end of said body structure comprising a microdevice for perforating only the skin's stratum corneum layer for intraepidermal delivery of active agents and at least one built-in non-verbal instructional device to elicit correct behavior, rectify incorrect behavior and improve user compliance by producing instructional signals signifying one or more of the number of applications, the force of each application to validate each application, and the duration of each application;
said second end of said body structure comprising an active agent reservoir containing at least one active agent and an active agent applicator portion configured to release the active agent directly onto the perforated skin.

* * * * *